United States Patent
Hill

(10) Patent No.: US 9,655,780 B2
(45) Date of Patent: May 23, 2017

(54) ENHANCEMENT OF AQUEOUS FLOW

(71) Applicant: Orange County Glaucoma, PC, Santa Ana, CA (US)

(72) Inventor: Richard A. Hill, Irvine, CA (US)

(73) Assignee: Orange County Glaucoma, PC, Santa Ana, CA (US)

( * ) Notice: Subject to any disclaimer, the term of this patent is extended or adjusted under 35 U.S.C. 154(b) by 0 days.

(21) Appl. No.: 14/848,030

(22) Filed: Sep. 8, 2015

(65) Prior Publication Data

US 2015/0374546 A1    Dec. 31, 2015

Related U.S. Application Data

(63) Continuation of application No. PCT/US2014/029657, filed on Mar. 14, 2014.

(60) Provisional application No. 61/793,241, filed on Mar. 15, 2013.

(51) Int. Cl.
| | |
|---|---|
| *A61M 5/00* | (2006.01) |
| *A61F 9/007* | (2006.01) |
| *A61F 9/00* | (2006.01) |
| *A61F 2/94* | (2013.01) |

(52) U.S. Cl.
CPC ........ *A61F 9/00781* (2013.01); *A61F 9/0017* (2013.01); *A61F 2/94* (2013.01); *A61F 9/0008* (2013.01)

(58) Field of Classification Search
CPC . A61F 9/00781; A61F 9/0017; A61K 9/0051; A61K 31/5575; A61K 47/32; A61K 47/02; A61B 3/16
USPC ............................................................ 604/9
See application file for complete search history.

(56) References Cited

U.S. PATENT DOCUMENTS

| | | | | |
|---|---|---|---|---|
| 5,397,300 | A * | 3/1995 | Baerveldt | A61F 9/00781 604/10 |
| 7,094,225 | B2 * | 8/2006 | Tu | A61F 9/00781 604/290 |
| 7,163,543 | B2 * | 1/2007 | Smedley | A61F 9/0017 606/107 |
| 7,273,475 | B2 * | 9/2007 | Tu | A61F 9/00781 604/290 |
| 7,331,984 | B2 * | 2/2008 | Tu | A61F 9/00781 128/898 |
| 7,431,710 | B2 * | 10/2008 | Tu | A61F 9/00781 604/8 |

(Continued)

FOREIGN PATENT DOCUMENTS

| | | |
|---|---|---|
| WO | WO-2010/093945 A2 | 8/2010 |
| WO | WO-2012/071476 A2 | 5/2012 |

OTHER PUBLICATIONS

Extended European Search Report dated Nov. 9, 2016, which issued in European Application No. 14765197.0.

*Primary Examiner* — Philip R Wiest
(74) *Attorney, Agent, or Firm* — Nathan S. Smith; McDermott Will & Emery LLP

(57) ABSTRACT

Drainage of body fluid from an area of undesirably high pressure can be accomplished by interconnecting an artificial non-blood fluid conduit with the vascular system. For example, an artificial non-blood fluid conduit can be inserted into the eye to fluidly interconnect the anterior chamber with a location of lower pressure. The conduit can have a growth factor for stimulating growth of new blood vessels in the location of lower pressure to connect the new blood vessels with the non-blood fluid conduit.

23 Claims, 17 Drawing Sheets

(56) References Cited

U.S. PATENT DOCUMENTS

| | | | |
|---|---|---|---|
| 7,488,303 B1* | 2/2009 | Haffner | A61F 9/00781 604/521 |
| 7,708,711 B2* | 5/2010 | Tu | A61F 9/0017 604/264 |
| 7,867,186 B2* | 1/2011 | Haffner | 604/8 |
| 7,879,001 B2* | 2/2011 | Haffner | A61F 9/00781 604/27 |
| 7,879,079 B2* | 2/2011 | Tu | A61F 9/00781 128/898 |
| 7,951,155 B2* | 5/2011 | Smedley | A61F 9/0017 606/107 |
| 8,007,459 B2* | 8/2011 | Haffner | A61F 9/00781 604/8 |
| 8,337,445 B2* | 12/2012 | Tu | A61F 9/00781 604/10 |
| 8,506,515 B2* | 8/2013 | Burns | A61F 9/00781 604/8 |
| 8,617,094 B2* | 12/2013 | Smedley | A61F 9/00781 604/10 |
| 8,758,290 B2* | 6/2014 | Horvath | A61F 9/00781 604/8 |
| 8,882,781 B2* | 11/2014 | Smedley | A61F 9/0017 606/107 |
| 9,155,654 B2* | 10/2015 | Tu | A61F 9/00781 |
| 9,173,775 B2* | 11/2015 | Haffner | A61F 9/0017 |
| 9,220,632 B2* | 12/2015 | Smedley | A61F 9/00781 |
| 9,301,875 B2* | 4/2016 | Tu | A61F 9/00781 |
| 2005/0049578 A1* | 3/2005 | Tu | A61B 3/16 604/890.1 |
| 2007/0141116 A1 | 6/2007 | Pinchuk et al. | |
| 2007/0293872 A1 | 12/2007 | Peyman | |
| 2010/0234790 A1 | 9/2010 | Tu et al. | |
| 2011/0238075 A1* | 9/2011 | Clauson | A61F 9/0017 606/107 |

* cited by examiner

Sequence annotation (Features)

| Feature key | Positions(s) | Length | Description |
|---|---|---|---|
| Molecule Processing | | | |
| Signal peptide | 1-26 | 26 | Ref.22 Ref.23 Ref.24 |
| Chain | 27-232 | 206 | Vascular endothelial growth factor A |

*FIG. 15A*

| SEQ ID NO:1 | | Length | Mass(Da) |
|---|---|---|---|
| Isoform VEGF206 [UniParc]. | FASTA | 232 | 27,042 |

Last modified November 16, 2001. Version 2
Checksum: FB49F364446F4D01
Vascular endothelial growth factor A precursor – Homo sapiens (Human)

```
         10         20         30         40         50
 MNFLLSWVHW SLALLLYLHH AKWSQAAPMA EGGGQNHHEV VKFMDVYQRS
         60         70         80         90        100
 YCHPIETLVD IFQEYPDEIE YIFKPSCVPL MRCGGCCNDE GLECVPTEES
        110        120        130        140        150
 NITMQIMRIK PHQGQHIGEM SFLQHNKCEC RPKKDRARQE KKSVRGKGKG
        160        170        180        190        200
 QKRKRKKSRY KSWSVYVGAR CCLMPWSLPG PHPCGPCSER RKHLFVQDPQ
        210        220        230
 TCKCSCKNTD SRCKARQLEL NERTCRCDKP RR
```

*FIG. 15B*

| SEQ ID NO:2 | | Length | Mass(Da) |
|---|---|---|---|
| Isoform VEGF189 [UniParc]. | FASTA | 215 | 25,173 |

Checksum: 7B9759AD5971FF33

```
         10         20         30         40         50
 MNFLLSWVHW SLALLLYLHH AKWSQAAPMA EGGGQNHHEV VKFMDVYQRS
         60         70         80         90        100
 YCHPIETLVD IFQEYPDEIE YIFKPSCVPL MRCGGCCNDE GLECVPTEES
        110        120        130        140        150
 NITMQIMRIK PHQGQHIGEM SFLQHNKCEC RPKKDRARQE KKSVRGKGKG
        160        170        180        190        200
 QKRKRKKSRY KSWSVPCGPC SERRKHLFVQ DPQTCKCSCK NTDSRCKARQ
        210
 LELNERTCRC DKPRR
```

*FIG. 15C*

SEQ ID NO:3　　　　　　　　　　　　　　　　Length　　Mass(Da)
Isoform VEGF183 [UniParc].　　　FASTA　　209　　　24,422
Checksum: F01CCEACD945D6CA

```
         10         20         30         40         50
   MNFLLSWVHW SLALLLYLHH AKWSQAAPMA EGGGQNHHEV VKFMDVYQRS
         60         70         80         90        100
   YCHPIETLVD IFQEYPDEIE YIFKPSCVPL MRCGGCCNDE GLECVPTEES
        110        120        130        140        150
   NITMQIMRIK PHQGQHIGEM SFLQHNKCEC RPKKDRARQE KKSVRGKGKG
        160        170        180        190        200
   QKRKRKKSRP CGPCSERRKH LFVQDPQTCK CSCKNTDSRC KARQLELNER

TCRCDKPRR
```

*FIG. 15D*

SEQ ID NO:4　　　　　　　　　　　　　　　　Length　　Mass(Da)
Isoform VEGF165 (VEGF) [UniParc].　FASTA　　191　　　22,314
Checksum: CCE57097DD3779BD

```
         10         20         30         40         50
   MNFLLSWVHW SLALLLYLHH AKWSQAAPMA EGGGQNHHEV VKFMDVYQRS
         60         70         80         90        100
   YCHPIETLVD IFQEYPDEIE YIFKPSCVPL MRCGGCCNDE GLECVPTEES
        110        120        130        140        150
   NITMQIMRIK PHQGQHIGEM SFLQHNKCEC RPKKDRARQE NPCGPCSERR
        160        170        180        190
   KHLFVQDPQT CKCSCKNTDS RCKARQLELN ERTCRCDKPR R
```

*FIG. 15E*

SEQ ID NO:5　　　　　　　　　　　　　　　　　　　　　Length　　Mass(Da)
Isoform VEGF148 [UniParc].　　　　　FASTA　　174　　20,218
Checksum: AE88400CA7757644

```
         10         20         30         40         50
     MNFLLSWVHW SLALLLYLHH AKWSQAAPMA EGGGQNHHEV VKFMDVYQRS
         60         70         80         90        100
     YCHPIETLVD IFQEYPDEIE YIFKPSCVPL MRCGGCCNDE GLECVPTEES
        110        120        130        140        150
     NITMQIMRIK PHQGQHIGEM SFLQHNKCEC RPKKDRARQE NPCGPCSERR
        160        170
     KHLFVQDPQT CKCSCKNTDS RCKM
```

*FIG. 15F*

SEQ ID NO:6　　　　　　　　　　　　　　　　　　　　　Length　　Mass(Da)
Isoform VEGF145 [UniParc].　　　　　FASTA　　171　　20,064
Checksum: D02ECA735FF6E9F8

```
         10         20         30         40         50
     MNFLLSWVHW SLALLLYLHH AKWSQAAPMA EGGGQNHHEV VKFMDVYQRS
         60         70         80         90        100
     YCHPIETLVD IFQEYPDEIE YIFKPSCVPL MRCGGCCNDE GLECVPTEES
        110        120        130        140        150
     NITMQIMRIK PHQGQHIGEM SFLQHNKCEC RPKKDRARQE KKSVRGKGKG
        160        170
     QKRKRKKSRY KSWSVCDKPR R
```

*FIG. 15G*

SEQ ID NO:7　　　　　　　　　　　　　　　　　　　　　Length　　Mass(Da)
Isoform VEGF165B [UniParc].　　　　FASTA　　191　　22,259
Checksum: D25243E540AC79BD

```
         10         20         30         40         50
     MNFLLSWVHW SLALLLYLHH AKWSQAAPMA EGGGQNHHEV VKFMDVYQRS
         60         70         80         90        100
     YCHPIETLVD IFQEYPDEIE YIFKPSCVPL MRCGGCCNDE GLECVPTEES
        110        120        130        140        150
     NITMQIMRIK PHQGQHIGEM SFLQHNKCEC RPKKDRARQE NPCGPCSERR
        160        170        180        190
     KHLFVQDPQT CKCSCKNTDS RCKARQLELN ERTCRSLTRK D
```

*FIG. 15H*

SEQ ID NO:8  
Isoform VEGF121 [UniParc].  FASTA  
Checksum: DDF4D6994249BED6

| | Length | Mass(Da) |
|---|---|---|
| | 147 | 17,219 |

```
         10         20         30         40         50
  MNFLLSWVHW SLALLLYLHH AKWSQAAPMA EGGGQNHHEV VKFMDVYQRS
         60         70         80         90        100
  YCHPIETLVD IFQEYPDEIE YIFKPSCVPL MRCGGCCNDE GLECVPTEES
        110        120        130        140
  NITMQIMRIK PHQGQHIGEM SFLQHNKCEC RPKKDRARQE KCDKPRR
```

*FIG. 15I*

SEQ ID NO:9  
Isoform VEGF111 [UniParc].  FASTA  
Checksum: 196B2BB49381BE87

| | Length | Mass(Da) |
|---|---|---|
| | 137 | 15,981 |

```
         10         20         30         40         50
  MNFLLSWVHW SLALLLYLHH AKWSQAAPMA EGGGQNHHEV VKFMDVYQRS
         60         70         80         90        100
  YCHPIETLVD IFQEYPDEIE YIFKPSCVPL MRCGGCCNDE GLECVPTEES
        110        120        130
  NITMQIMRIK PHQGQHIGEM SFLQHNKCEC RCDKPRR
```

*FIG. 15J*

SEQ ID NO:10  
Isoform L-VEGF165 [UniParc].  FASTA  
Checksum: 053E9CA56725C07B

| | Length | Mass(Da) |
|---|---|---|
| | 371 | 40,738 |

```
         10         20         30         40         50
  MTDRQTDTAP SPSYHLLPGR RRTVDAAASR GQGPEPAPGG GVEGVGARGV
         60         70         80         90        100
  ALKLFVQLLG CSRFGGAVVR AGEAEPSGAA RSASSGREEP QPEEGEEEEE
        110        120        130        140        150
  KEEERGPQWR LGARKPGSWT GEAAVCADSA PAARAPQALA RASGRGGRVA
        160        170        180        190        200
  RRGAEESGPP HSPSRRGSAS RAGPGRASET MNFLLSWVHW SLALLLYLHH
        210        220        230        240        250
  AKWSQAAPMA EGGGQNHHEV VKFMDVYQRS YCHPIETLVD IFQEYPDEIE
        260        270        280        290        300
  YIFKPSCVPL MRCGGCCNDE GLECVPTEES NITMQIMRIK PHQGQHIGEM
        310        320        330        340        350
  SFLQHNKCEC RPKKDRARQE NPCGPCSERR KHLFVQDPQT CKCSCKNTDS
        360        370
  RCKARQLELN ERTCRCDKPR R
```

*FIG. 15K*

SEQ ID NO:11
Isoform L-VEGF121 [UniParc].  FASTA  Length 327  Mass(Da) 35,643
Checksum: 8D6F969601B2A9EF

```
         10         20         30         40         50
 MTDRQTDTAP SPSYHLLPGR RRTVDAAASR GQGPEPAPGG GVEGVGARGV
         60         70         80         90        100
 ALKLFVQLLG CSRFGGAVVR AGEAEPSGAA RSASSGREEP QPEEGEEEEE
        110        120        130        140        150
 KEEERGPQWR LGARKPGSWT GEAAVCADSA PAARAPQALA RASGRGGRVA
        160        170        180        190        200
 RRGAEESGPP HSPSRRGSAS RAGPGRASET MNFLLSWVHW SLALLLYLHH
        210        220        230        240        250
 AKWSQAAPMA EGGGQNHHEV VKFMDVYQRS YCHPIETLVD IFQEYPDEIE
        260        270        280        290        300
 YIFKPSCVPL MRCGGCCNDE GLECVPTEES NITMQIMRIK PHQGQHIGEM
        310        320
 SFLQHNKCEC RPKKDRARQE KCDKPRR
```

*FIG. 15L*

SEQ ID NO:12
Isoform L-VEGF189 [UniParc].  FASTA  Length 395  Mass(Da) 43,597
Checksum: 8ADF6524B1835A2D

```
         10         20         30         40         50
 MTDRQTDTAP SPSYHLLPGR RRTVDAAASR GQGPEPAPGG GVEGVGARGV
         60         70         80         90        100
 ALKLFVQLLG CSRFGGAVVR AGEAEPSGAA RSASSGREEP QPEEGEEEEE
        110        120        130        140        150
 KEEERGPQWR LGARKPGSWT GEAAVCADSA PAARAPQALA RASGRGGRVA
        160        170        180        190        200
 RRGAEESGPP HSPSRRGSAS RAGPGRASET MNFLLSWVHW SLALLLYLHH
        210        220        230        240        250
 AKWSQAAPMA EGGGQNHHEV VKFMDVYQRS YCHPIETLVD IFQEYPDEIE
        260        270        280        290        300
 YIFKPSCVPL MRCGGCCNDE GLECVPTEES NITMQIMRIK PHQGQHIGEM
        310        320        330        340        350
 SFLQHNKCEC RPKKDRARQE KKSVRGKGKG QKRKRKKSRY KSWSVPCGPC
        360        370        380        390
 SERRKHLFVQ DPQTCKCSCK NTDSRCKARQ LELNERTCRC DKPRR
```

*FIG. 15M*

SEQ ID NO:13　　　　　　　　　　　　　　　　Length　　Mass(Da)
Isoform L-VEGF206 [UniParc].　　　FASTA　　412　　　45,467
Checksum: AC807D3F21528D35

```
              10         20         30         40         50
         MTDRQTDTAP SPSYHLLPGR RRTVDAAASR GQGPEPAPGG GVEGVGARGV
              60         70         80         90        100
         ALKLFVQLLG CSRFGGAVVR AGEAEPSGAA RSASSGREEP QPEEGEEEEE
             110        120        130        140        150
         KEEERGPQWR LGARKPGSWT GEAAVCADSA PAARAPQALA RASGRGGRVA
             160        170        180        190        200
         RRGAEESGPP HSPSRRGSAS RAGPGRASET MNFLLSWVHW SLALLLYLHH
             210        220        230        240        250
         AKWSQAAPMA EGGGQNHHEV VKFMDVYQRS YCHPIETLVD IFQEYPDEIE
             260        270        280        290        300
         YIFKPSCVPL MRCGGCCNDE GLECVPTEES NITMQIMRIK PHQGQHIGEM
             310        320        330        340        350
         SFLQHNKCEC RPKKDRARQE KKSVRGKGKG QKRKRKKSRY KSWSVYVGAR
             360        370        380        390        400
         CCLMPWSLPG PHPCGPCSER RKHLFVQDPQ TCKCSCKNTD SRCKARQLEL
             410
         NERTCRCDKP RR
```

*FIG. 15N*

| Sequence annotation (Features) | | | | | |
|---|---|---|---|---|---|
| Feature key | Positions(s) | Length | Description | Graphical view | Feature identifier |
| Molecule processing | | | | | |
| Signal peptide | 1-21 | 21 | Potential | I | |
| Chain | 22-207 | 186 | Vascular endothelial growth factor B | I | PRO_0000023398 |

FIG. 16A

SEQ ID NO:14  Length  Mass(Da)
Isoform VEGF-B186 [UniParc].  FASTA  207  21,602
Last modified November 16, 2001. Version 2.
Checksum: EDE4B1C0DFDAD6BC

```
          10         20         30         40         50
    MSPLLRRLLL AALLQLAPAQ APVSQPDAPG HQRKVVSWID VYTRATCQPR
          60         70         80         90        100
    EVVVPLTVEL MGTVAKQLVP SCVTVQRCGG CCPDDGLECV PTGQHQVRMQ
         110        120        130        140        150
    ILMIRYPSSQ LGEMSLEEHS QCECRPKKKD SAVKPDRAAT PHHRPQPRSV
         160        170        180        190        200
    PGWDSAPGAP SPADITHPTP APGPSAHAAP STTSALTPGP AAAAADAAAS

SVAKGGA
```

FIG. 16B

SEQ ID NO:15  Length  Mass(Da)
Isoform VEGF-B167 [UniParc].  FASTA  188  21,261
Checksum: F04654D5A3727194

```
          10         20         30         40         50
    MSPLLRRLLL AALLQLAPAQ APVSQPDAPG HQRKVVSWID VYTRATCQPR
          60         70         80         90        100
    EVVVPLTVEL MGTVAKQLVP SCVTVQRCGG CCPDDGLECV PTGQHQVRMQ
         110        120        130        140        150
    ILMIRYPSSQ LGEMSLEEHS QCECRPKKKD SAVKPDSPRP LCPRCTQHHQ
         160        170        180
    RPDPRTCRRR CRRRSFLRCQ GRGLELNPDT CRCRKLRR
```

FIG. 16C

| Sequence annotation (Features) | | | | | |
|---|---|---|---|---|---|
| Feature key | Positions(s) | Length | Description | Graphical view | Feature identifier |
| Molecule processing | | | | | |
| Signal peptide | 1-31 | 31 | Ref.9 Ref.10 | I | |
| Propeptide | 32-111 | 80 | Or 102 | I I | PRO_0000023400 |
| Chain | 112-227 | 116 | Vascular endothelial growth factor C | I I | PRO_0000023401 |
| Propeptide | 228-419 | 192 | | I | PRO_0000023402 |

*FIG. 17A*

SEQ ID NO:16
P49767 [UniParc].                                    FASTA    Length 419    Mass(Da) 46,883
Last modified October 1, 1996. Version 1.
Checksum: 9F598719DB3E014F

```
            10         20         30         40         50
    MHLLGFFSVA CSLLAAALLP GPREAPAAAA AFESGLDLSD AEPDAGEATA
            60         70         80         90        100
    YASKDLEEQL RSVSSVDELM TVLYPEYWKM YKCQLRKGGW QHNREQANLN
           110        120        130        140        150
    SRTEETIKFA AAHYNTEILK SIDNEWRKTQ CMPREVCIDV GKEFGVATNT
           160        170        180        190        200
    FFKPPCVSVY RCGGCCNSEG LQCMNTSTSY LSKTLFEITV PLSQGPKPVT
           210        220        230        240        250
    ISFANHTSCR CMSKLDVYRQ VHSIIRRSLP ATLPQCQAAN KTCPTNYMWN
           260        270        280        290        300
    NHICRCLAQE DFMFSSDAGD DSTDGFHDIC GPNKELDEET CQCVCRAGLR
           310        320        330        340        350
    PASCGPHKEL DRNSCQCVCK NKLFPSQCGA NREFDENTCQ CVCKRTCPRN
           360        370        380        390        400
    QPLNPGKCAC ECTESPQKCL LKGKKFHHQT CSCYRRPCTN RQKACEPGFS
           410
    YSEEVCRCVP SYWKRPQMS
```

*FIG. 17B*

Sequence annotation (Features)

| Feature key | Positions(s) | Length | Description | Graphical view | Feature identifier |
|---|---|---|---|---|---|
| Molecule processing | | | | | |
| Signal peptide | 1-21 | 21 | Potential | I | |
| Propeptide | 22-88 | 67 | Or 99 | I I | PRO_0000023408 |
| Chain | 89-205 | 117 | Vascular endothelial growth factor D | I I | PRO_0000023409 |
| Propeptide | 206-354 | 149 | | I | PRO_0000023410 |

FIG. 18A

SEQ ID NO:17
O43915 [UniParc].                        FASTA    Length 354    Mass(Da) 40,444
Last modified June 1, 1998. Version 1
Checksum: 2048D769D735173E

```
            10         20         30         40         50
     MYREWVVVNV FMMLYVQLVQ GSSNEHGPVK RSSQSTLERS EQQIRAASSL
            60         70         80         90        100
     EELLRITHSE DWKLWRCRLR LKSFTSMDSR SASHRSTRFA ATFYDIETLK
           110        120        130        140        150
     VIDEEWQRTQ CSPRETCVEV ASELGKSTNT FFKPPCVNVF RCGGCCNEES
           160        170        180        190        200
     LICMNTSTSY ISKQLFEISV PLTSVPELVP VKVANHTGCK CLPTAPRHPY
           210        220        230        240        250
     SIIRRSIQIP EEDRCSHSKK LCPIDMLWDS NKCKCVLQEE NPLAGTEDHS
           260        270        280        290        300
     HLQEPALCGP HMMFDEDRCE CVCKTPCPKD LIQHPKNCSC FECKESLETC
           310        320        330        340        350
     CQKHKLFHPD TCSCEDRCPF HTRPCASGKT ACAKHCRFPK EKRAAQGPHS

RKNP
```

FIG. 18B

ENHANCEMENT OF AQUEOUS FLOW

CROSS-REFERENCE TO RELATED APPLICATIONS

This application is a continuation of PCT Application Serial No. PCT/US2014/029657, filed on Mar. 14, 2014, designating the United States and published in English, which claims the priority and benefit under 35 U.S.C. §119(e) of U.S. Provisional Application Ser. No. 61/793,241, filed Mar. 15, 2013, the entirety of each of which is hereby incorporated herein by reference.

CROSS-REFERENCE TO A SEQUENCE LISTING

A Sequence Listing is being submitted electronically via EFS in the form of a text file, created Sep. 4, 2015, and named 0928240017seqlist.txt (37335 bytes), the contents of which are incorporated herein by reference in their entirety.

BACKGROUND

Field of the Inventions

The present inventions relate to the enhancement of flow from a first area to a second area, which can be an area of lower pressure, in the body. More specifically, the present disclosure relates to aqueous flow, such as for treating glaucoma using pumping devices and/or a growth factor to stimulate blood vessel growth to fluidly interconnect an outflow portion of an implant, placed in the eye, with a drainage pathway.

Description of the Related Art

Aqueous humor is a transparent fluid that is secreted from the ciliary epithelium between the anterior and posterior chambers of the eye. One natural flow of aqueous humor in the eye is into the anterior chamber and out of the anterior chamber through the trabecular meshwork. It then passes through Schlemm's canal to be collected in channels at the back of Schlemm's canal. These collector channels gather together and form episcleral veins, which carry the aqueous humor out into the venous system to be circulated into the bloodstream.

SUMMARY

According to some embodiments, an intraocular implant can be provided that is configured to facilitate or stimulate blood vessel growth in order to fluidly interconnect the implant with a plurality of new blood vessels. The implant can comprise an inflow region or shunt that can be positioned in fluid communication with (e.g., extending into) the anterior chamber on the surface of the eye and an outflow region or shunt extending into a region of lower pressure of the eye, such as a subconjunctival space, a suprachoroidal space, or a supraciliary space of the eye.

In some embodiments, the methods and apparatuses disclosed herein provide a manner of facilitating outflow of aqueous humor through an implant from the anterior chamber to a location of lower pressure by developing new episcleral veins adjacent to an outlet portion of the implant in the location of lower pressure.

In some embodiments, methods and apparatuses are provided for fluidly interconnecting blood vessels with non-blood artificial conduits.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1 or clause 5. The other clauses can be presented in a similar manner.

Clause 1. An intraocular implant comprising: a first tubular member having an inlet and an outlet; a pump body having an inlet and an outlet, the inlet being in fluid communication with the first tubular member outlet, the pump body further comprising a pumping chamber configured to resiliently expand from a compressed state to create a suction force at the first tubular member inlet, the pump body being compressible to expel fluid from the pump body outlet; a first one-way valve coupled to the first tubular member for permitting inflow into the first tubular member inlet and into the pump body inlet; a second tubular member having an inlet and an outlet, the inlet being in fluid communication with the pump body outlet to receive expelled fluid therefrom; and a second one-way valve coupled to the second tubular member for permitting flow into the second tubular member inlet and out through the second tubular member outlet.

Clause 2. The implant of Clause 1, wherein the first one-way valve is positioned adjacent to the first tubular member outlet.

Clause 3. The implant of any of Clauses 1 to 2, wherein the second one-way valve is positioned adjacent to the second tubular member inlet.

Clause 4. The implant of any of Clauses 1 to 3, wherein the pump body comprises a pumping surface area of from about 1 mm$^2$ to about 40 mm$^2$.

Clause 5. The implant of any of Clauses 1 to 4, wherein the second tubular member comprises a growth factor.

Clause 6. The implant of Clause 5, wherein the growth factor is coated onto an outlet portion of the second tubular member.

Clause 7. The implant of Clause 5, wherein the second tubular member comprises an outlet portion formed from a resorbable material, and wherein the growth factor is impregnated into the resorbable material.

Clause 8. The implant of any of Clauses 1 to 7, wherein the pump body is compressible using a pulsed pressure of at least 7 mm Hg.

Clause 9. The implant of Clause 8, wherein the pump body is compressible using a pulsed pressure of at least 10 mm Hg.

Clause 10. The implant of Clause 9, wherein the pump body is compressible using a pulsed pressure of at least 13 mm Hg.

Clause 11. The implant of any of Clauses 1 to 10, wherein the first tubular member is configured to be inserted into an anterior chamber of an eye, and the second tubular member is configured to extend through a trabecular meshwork and/or sclera of the eye to an outflow space.

Clause 12. The implant of any of Clauses 1 to 11, wherein the outflow space comprises at least one of a supraciliary space, an intrascleral space, a suprachoroidal space, a subconjunctival space, episcleral veins, aqueous collector channels, or Schlemm's canal.

Clause 13. An intraocular implant comprising: a tubular member having an inlet region configured to extend into an anterior chamber of an eye, and a vascular connecting outlet region (i) extending along a portion of the tubular member and configured to extend into an outflow space comprising at least one of a supraciliary space, an intrascleral space, a suprachoroidal space, a subconjunctival space, episcleral veins, aqueous collector channels, or Schlemm's canal; and a growth factor carried by the vascular connecting outlet region.

Clause 14. The implant of Clause 13, wherein the vascular connecting region comprises at least about half of a length of the tubular member.

Clause 15. The implant of any of Clauses 13 to 14, wherein the vascular connecting region comprises at least about a third of a length of the tubular member.

Clause 16. The implant of any of Clauses 13 to 15, wherein the vascular connecting region comprises at least about a fourth of a length of the tubular member.

Clause 17. The implant of any of Clauses 13 to 16, wherein the vascular connecting region comprises at least about a fifth of a length of the tubular member.

Clause 18. The implant of any of Clauses 13 to 17, wherein the vascular connecting region comprises at less than about a fifth of a length of the tubular member.

Clause 19. The implant of any of Clauses 13 to 18, wherein the vascular connecting region comprises a plurality of recesses configured to carry the growth factor therein.

Clause 20. The implant of any of Clauses 13 to 19, wherein the growth factor comprises a vascular growth factor.

Clause 21. The implant of Clause 20, wherein the growth factor comprises a VEGF.

Clause 22. The implant of any of Clauses 13 to 21, wherein the vascular connecting region comprises a resorbable material and a least a portion of the growth factor.

Clause 23. The implant of Clause 22, wherein the vascular connecting region comprises a non-resorbable polymeric material and a plurality of apertures extending in a direction transverse to the stent lumen, the plurality of apertures comprising a resorbable material and the growth factor disposed therein.

Clause 24. The implant of Clause 23, wherein the plurality of apertures extend along an entire length of the vascular connecting region.

Clause 25. The implant of any of Clauses 13 to 24, wherein the vascular connecting region is formed from a resorbable material, and the growth factor is impregnated into the resorbable material.

Clause 26. The implant of any of Clauses 13 to 25, wherein the growth factor comprises a coating on the vascular connecting region.

Clause 27. The implant of any of Clauses 13 to 26, further comprising a pump for urging fluid through the implant.

Clause 28. The implant of Clause 27, wherein the pump is configured to operate using ocular pulse pressure.

Clause 29. The implant of Clause 28, wherein the pump comprises a one-way valve.

Clause 30. The implant of any of Clauses 13 to 29, further comprising a one-way valve for facilitating fluid flow through the implant.

Clause 31. An intraocular implant comprising: a tubular member having an inlet region configured to extend into an anterior chamber of an eye, and a vascular connecting outlet region (i) extending along a portion of the tubular member and configured to extend into an outflow space comprising at least one of a supraciliary space, an intrascleral space, a suprachoroidal space, a subconjunctival space, episcleral veins, aqueous collector channels, or Schlemm's canal; and a pump mechanism fluidly coupled to the inlet region, the pump mechanism having a pumping chamber that defines a pumping surface area of from about 1 mm$^2$ to about 40 mm$^2$.

Clause 32. The implant of Clause 31, wherein the pumping surface area is from about 1 mm$^2$ to about 25 mm$^2$.

Clause 33. The implant of any of Clauses 31 to 32, wherein the pumping surface area is from about 1 mm$^2$ to about 15 mm$^2$.

Clause 34. The implant of any of Clauses 31 to 33, wherein the pumping surface area is from about 1 mm$^2$ to about 10 mm$^2$.

Clause 35. A method of deploying an intraocular implant into an eye for stimulating vascular growth, the method comprising: inserting into the eye a deployment member carrying the implant; releasing the implant from the deployment member such that an inflow region of the implant resides in a higher pressure chamber of the eye and a vascular connecting region of the implant resides in a location of lower pressure chamber of the eye, the implant having a lumen to conduct fluid therethrough, the vascular connecting region of the implant carrying a growth factor for promoting growth of blood vessels adjacent to the vascular connecting region within the lower pressure chamber to facilitate aqueous humor outflow from the higher pressure chamber; and withdrawing the deployment member from the eye.

Clause 36. The method of Clause 35, wherein the growth factor comprises a vascular growth factor selected from the group consisting of a VEGF isoform.

Clause 37. The method of any of Clauses 35 to 36, wherein the growth factor comprises a VEGF.

Clause 38. The method of any of Clauses 35 to 37, wherein the lower pressure chamber comprises at least one of a supraciliary space, an intrascleral space, a suprachoroidal space, a subconjunctival space, episcleral veins, aqueous collector channels, or Schlemm's canal.

Clause 39. The method of any of Clauses 35 to 38, wherein the higher pressure chamber comprises the anterior chamber.

Clause 40. The method of any of Clauses 35 to 39, wherein the vascular connecting region comprises a resorbable material and a least a portion of the growth factor.

Clause 41. The method of Clause 40, wherein the vascular connecting region comprises a non-resorbable polymeric material having a plurality of apertures extending in a direction transverse to the stent lumen, the plurality of apertures comprising a resorbable material and the growth factor disposed therein.

Clause 42. The method of any of Clauses 40 to 41, wherein the growth factor is impregnated into the resorbable material.

Clause 43. The method of any of Clauses 35 to 42, wherein the growth factor is impregnated into the vascular connecting region.

Clause 44. The method of Clause 43, wherein the vascular connecting region comprises a resorbable material.

Clause 45. The method of any of Clauses 35 to 44, wherein the growth factor comprises a coating on the vascular connecting region.

Clause 46. A method of placing an intraocular implant for stimulating vascular growth, the method comprising implanting the implant into the eye such that a non-resorbable portion of the implant resides in a higher pressure chamber of the eye and a resorbable portion resides in a location of lower pressure chamber of the eye, the implant having a lumen extending therethrough, the resorbable portion comprising a growth factor for stimulating growth of new blood vessels, the resorbable portion configured to dissolve such that the new blood vessels converge toward the implant non-resorbable portion extending from the higher pressure chamber of the eye thereby enabling the implant lumen to be in fluid communication with the new blood vessels to facilitate aqueous humor outflow from the higher pressure chamber.

Clause 47. The method of Clause 46, wherein the growth factor comprises a vascular growth factor.

Clause 48. The method of Clause 47, wherein the growth factor comprises a VEGF.

Clause 49. The method of any of Clauses 46 to 48, wherein the lower pressure chamber comprises at least one of a supraciliary space, an intrascleral space, a suprachoroidal space, a subconjunctival space, episcleral veins, aqueous collector channels, or Schlemm's canal, and the growth factor promotes growth of episcleral veins.

Clause 50. The method of any of Clauses 46 to 49, wherein the higher pressure chamber comprises the anterior chamber.

Clause 51. A method of facilitating drainage of aqueous humor from a higher pressure chamber to a lower pressure chamber of an eye, the method comprising inserting an artificial non-blood fluid conduit into the eye to fluidly interconnects the higher pressure chamber with the lower pressure chamber, the conduit having a growth factor for stimulating growth of new blood vessels adjacent the lower pressure chamber to connect the new blood vessels with the non-blood fluid conduit.

Clause 52. The method of Clause 51, wherein the higher pressure chamber comprises the anterior chamber.

Clause 53. The method of any of Clauses 51 to 52, wherein the lower pressure chamber comprises at least one of a supraciliary space, an intrascleral space, a suprachoroidal space, a subconjunctival space, episcleral veins, aqueous collector channels, or Schlemm's canal.

Clause 54. A method of deploying an intraocular implant into an eye, the method comprising: inserting into the eye a deployment member carrying the implant of any of Clauses 1 to 34; releasing the implant from the deployment member such that (i) an inflow region of the implant resides in an anterior chamber of the eye, (ii) a pump body is positioned in subconjunctival space, and (iii) an outflow region resides in the subconjunctival space; and withdrawing the deployment member from the eye.

Clause 55. The method of Clause 54, wherein the inserting comprises piercing the cornea to perform the method ab interno.

Clause 56. The method of any of Clauses 54 to 55, wherein the inserting comprises advancing the deployment member through sclera to perform the method ab externo.

Clause 57. The method of any of Clauses 54 to 56, wherein the releasing comprises positioning the pump body between the cornea and a rectus muscle of the eye.

Clause 58. The method of any of Clauses 54 to 58, wherein the outflow region comprises a growth factor.

Clause 59. The method of Clause 58, wherein the growth factor comprises a VEGF.

Clause 60. The method of any of Clauses 54 to 59, wherein the higher pressure chamber comprises the anterior chamber.

Clause 61. The method of any of Clauses 54 to 60, wherein the lower pressure chamber comprises at least one of a supraciliary space, an intrascleral space, a suprachoroidal space, a subconjunctival space, episcleral veins, aqueous collector channels, or Schlemm's canal.

Clause 62. An implant comprising any of the features or structures disclosed herein.

Clause 63. A method of placing an implant comprising: placing an implant having any of the features or structures disclosed herein; and placing the implant to interconnect any of the bodily spaces disclosed herein with a location of lower pressure.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures:

FIGS. 15A-15N describe amino acid sequences for isoforms of VEGF A.

FIGS. 16A-16C describe amino acid sequences for isoforms of VEGF B.

FIGS. 17A-17B describe an amino acid sequence for VEGF C.

FIGS. 18A-18B describe an amino acid sequence for VEGF D.

DETAILED DESCRIPTION

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

Further, while the present description sets forth specific details of various embodiments, it will be appreciated that the description is illustrative only and should not be construed in any way as limiting. Furthermore, various applications of such embodiments and modifications thereto, which may occur to those who are skilled in the art, are also encompassed by the general concepts described herein.

Figure 1:
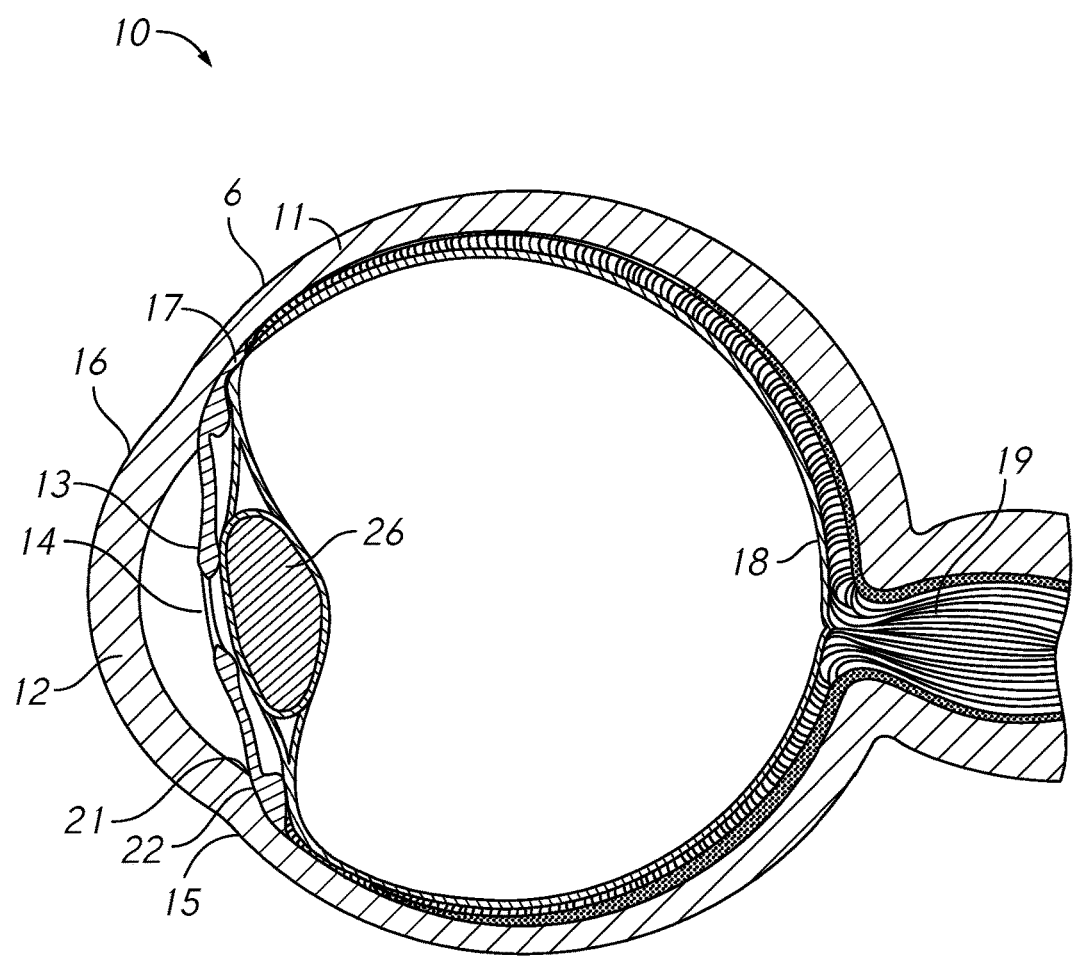
FIG. 1 is a cross-sectional view of an eye.

FIG. 1 illustrates a cross-sectional view of an eye 10. Thick collagenous tissue known as sclera 11 covers the entire eye 10 except that portion covered by the cornea 12. The cornea 12 is a thin transparent tissue that focuses and transmits light into the eye and the pupil 14 which is the circular hole in the center of the iris 13 (colored portion of the eye). The cornea 12 merges into the sclera 11 at a juncture referred to as the limbus 15. The conjunctiva 16 is a thin membrane that covers the sclera 11 and cornea 12. The ciliary epithelium begins internally in the eye and extends along the interior of the sclera 11 and becomes the choroid 17. The choroid 17 is a vascular layer of the eye underlying retina 18. The optic nerve 19 transmits visual information to the brain.

The anterior chamber 20 of the eye 10, which is bound anteriorly by the cornea 12 and posteriorly by the iris 13 and lens 26, is filled with aqueous humor. Aqueous humor is a transparent fluid that is secreted from the ciliary epithelium between the anterior and posterior chambers of the eye. The natural flow of aqueous humor in the eye is into the anterior chamber 20 and out of the anterior chamber through the trabecular meshwork 21. It then passes through Schlemm's canal 22 to be collected in channels at the back of Schlemm's canal 22. These collector channels gather together and form episcleral veins, which carry the aqueous humor out into the venous system to be circulated into the bloodstream.

Intraocular pressure of the eye 10 is maintained by the intricate balance of secretion and outflow of the aqueous in the manner described above. Glaucoma is characterized by the excessive buildup of aqueous fluid in the anterior chamber 20 which produces an increase in intraocular pressure (fluids are relatively incompressible and pressure is directed equally to all areas of the eye). The optic nerve 19 can be sequentially destroyed by glaucoma.

Implant Structures and Methods

Figure 2:
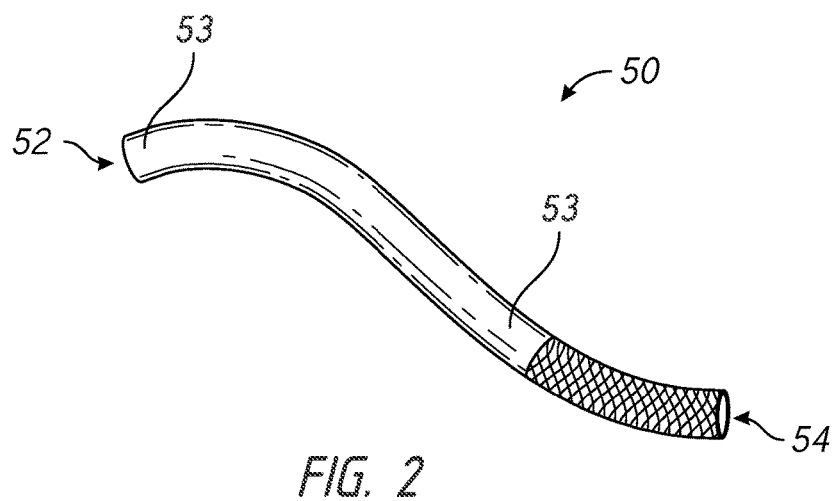
FIG. 2 is a perspective view of an implant, according to some embodiments.
Figure 3:
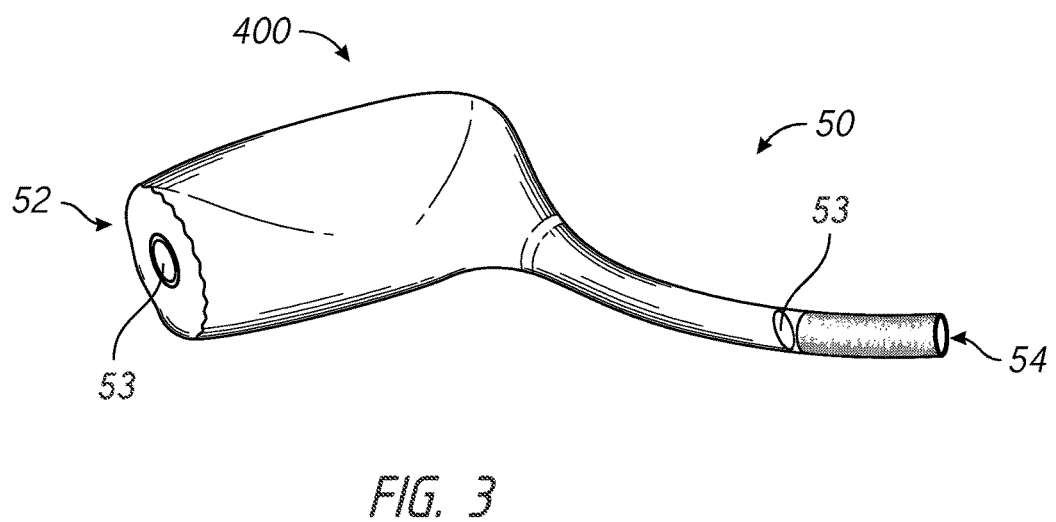
FIG. 3 is a perspective view of another implant having a pump mechanism, according to some embodiments.

According to some embodiments, an intraocular implant can be provided that is configured to facilitate or stimulate blood vessel growth in order to fluidly interconnect the implant with a plurality of new blood vessels. FIGS. 2-3 illustrate embodiments of implants 50, 60 that can comprise an inflow region 52, 62 that can be positioned in fluid communication with (e.g., extending into) the anterior chamber of the eye and a vascular connecting region 54, 64 extending into a region of lower pressure of the eye.

The implant 50, 60 can comprise a tubular or other shaped hollow member that can imbibe water. The implant 50, 60 can optionally comprise a porous material. The implant 50, 60 can be an aqueous transport member.

The vascular connecting region 54, 64 can be any suitable length or portion of the implant. In some embodiments, the vascular connecting region can extend externally, such as into the sclera.

In some embodiments, the methods and apparatuses disclosed herein provide a manner of facilitating outflow of aqueous humor through an implant from the anterior chamber to a location of lower pressure by developing new episcleral veins adjacent to the vascular connecting region of the implant in the location of lower pressure. The methods and apparatus can be inserted ab interno or ab externo. Ab interno surgery involves piercing the cornea and advancing the implant into the eye tissue, such as the anterior chamber angle or sclera, such that an inflow region of the implant resides in a higher pressure chamber and an outflow region resides in a lower pressure chamber. In contrast, ab externo surgery involves piercing the eye tissue, such as sclera, and advancing the implant through sclera and into fluid communication with the lower pressure chamber, such that an inflow region of the implant resides in a higher pressure chamber and an outflow region resides in a lower pressure chamber.

Growth Factors

Figure 4:
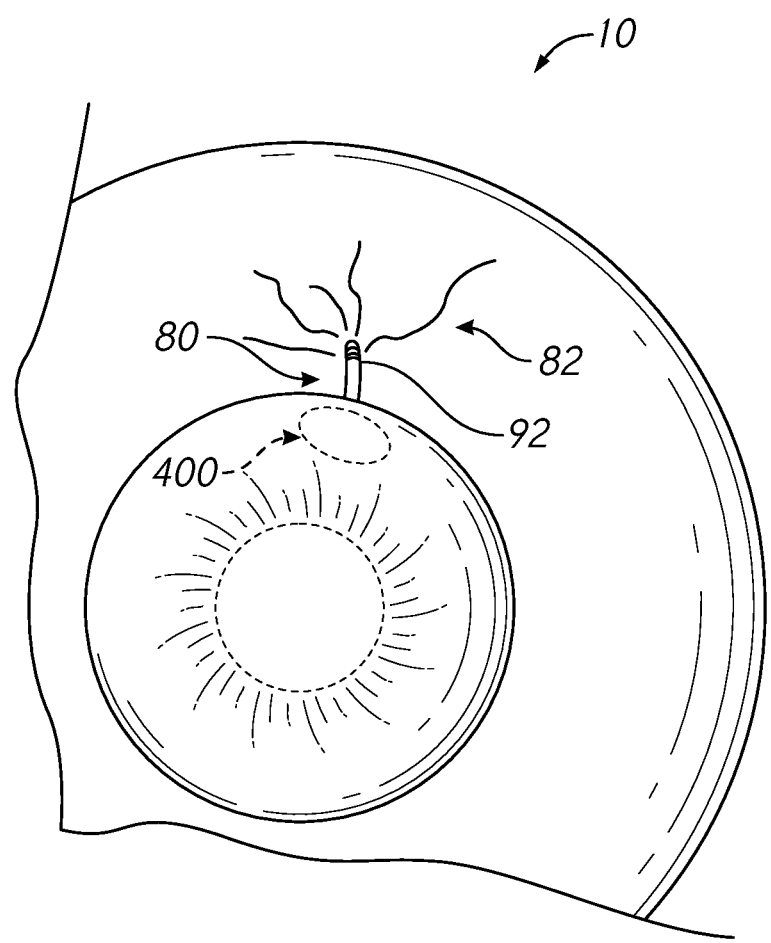
FIG. 4 is a schematic view of an implant implanted in an eye, according to some embodiments.

In accordance with some embodiments, the implant can comprise a growth factor. The growth factor can be carried by the implant, such as on an outflow portion or shunt, as a coating on the implant and/or incorporated into the material of the implant. As illustrated in FIG. 4, an implanted shunt 80 having a growth factor disposed thereon can stimulate growth of new blood vessels 82, as discussed herein.

In accordance with some embodiments, the growth factor can stimulate growth of blood vessels and/or aqueous collector channels.

FIG. 4 illustrates that, in some embodiments, the shunt 80 can comprise a vascular connecting region 92. The vascular connecting region 92 can comprise the growth factor. The vascular connecting region 92 can extend along an outlet end portion of the shunt. The vascular connecting region 92 can comprise any portion of the shunt, such as about one-half, one-third, one-fourth, one-fifth, one-sixth, one-seventh, or less of the overall shunt length.

In some embodiments, the growth factor can comprise a vascular endothelial growth factor (VEGF). VEGF is a sub-family of growth factors, and specifically, the platelet-derived growth factor family of cystine-knot growth factors. VEGF is an important signaling proteins involved in both vasculogenesis (the de novo formation of the embryonic circulatory system) and angiogenesis (the growth of blood vessels from pre-existing vasculature).

VEGF can be produced by certain organs to restore the oxygen supply to tissues when blood circulation is inadequate. For example, VEGF's normal function is to create new blood vessels during embryonic development, new blood vessels after injury, muscle following exercise, and new vessels (collateral circulation) to bypass blocked vessels.

For example, included within the family of VEGF, VEGF-A can facilitate angiogenesis, including the migration of endothelial cells, mitosis of endothelial cells, methane monooxygenase activity, $\alpha v \beta 3$ activity, creation of blood vessel lumens, creation of fenestrations, chemotactic for macrophages and granulocytes, and vasodilation (indirectly by NO release). Further, VEGF-B can facilitate embryonic angiogenesis (e.g., in myocardial tissue). VEGF-C can facilitate lymphangiogenesis. VEGF-D can facilitate the development of lymphatic vasculature surrounding lung bronchioles. Further, P1GF can facilitate vasculogenesis and be used for angiogenesis during ischemia, inflammation, wound healing, and cancer.

Further, the broad term VEGF covers a number of proteins from two families, that result from alternate splicing of mRNA from a single, 8-exon, VEGF gene. The two different families are referred to according to their terminal exon (exon 8) splice site—the proximal splice site (denoted VEGFxxx) or distal splice site (VEGFxxxb). In addition, alternate splicing of exon 6 and 7 alters their heparin-binding affinity, and amino acid number (in humans: VEGF121, VEGF121b, VEGF145, VEGF165, VEGF165b, VEGF189, VEGF206; the rodent orthologs of these proteins contain one fewer amino acid). These domains have important functional consequences for the VEGF splice variants, as the terminal (exon 8) splice site determines whether the proteins are pro-angiogenic (proximal splice site, expressed during angiogenesis) or anti-angiogenic (distal splice site, expressed in normal tissues). In addition, inclusion or exclusion of exons 6 and 7 mediate interactions with heparan sulfate proteoglycans (HSPGs) and neuropilin co-receptors on the cell surface, enhancing their ability to bind and activate the VEGF receptors (VEGFRs). Recently, VEGF-C has been shown to be an important inducer of neurogenesis in the murine subventricular zone, without exerting angiogenic effects.

However, VEGF can contribute to disease when it is overexpressed. For example, solid cancers cannot grow beyond a limited size without an adequate blood supply; cancers that can express VEGF are able to grow and metastasize. Further, overexpression of VEGF can contribute to macular degeneration, such as age-related macular degeneration (AMD) and vascular disease in the retina of the eye and other parts of the body.

Accordingly, although growth factors are known, the prior art does not teach the use of growth factors in the eye. Instead, the prior art teaches the use of drugs, such as anti-VEGF, in the eye to impede growth of blood vessels.

Anti-VEGF therapies are important to stop new blood vessel growth in cancers and in other eye diseases, such as diabetic retinopathy or macular degeneration. Such therapies can use drugs such as Ranibizumab (Lucentis™), Bevacizumab (Avastin®), lapatinib (Tykerb), sunitinib (Sutent), sorafenib (Nexavar), axitinib, pazopanib, THC, and Cannabidiol, can inhibit VEGF and control or slow cancers or diseases such as AMD. For example, Lucentis™ is an antibody that can be injected into the eye to bind to a VEGF, inactivate a VEGF, and stop new blood vessel growth. The use of products such as Lucentis™ allows a clinician to mitigate or prevent metastasizing of cancer cells. Accordingly, current thereapies for macular degeneration, for example, therefore relies on anti-VEGF thereapy.

Therefore, in the context of eye diseases, VEGF has been considered undesirable and therapy using growth factors such as a VEGF would not be considered desirable or obvious to a person of skill. As noted above, the body's own development of a VEGF in the eye occurs with disease, such as diabetic retinopathy and macular degeneration. In these diseases, the body forms new blood vessels on the retina. These blood vessels are bad because they can bleed, leak fluid, and cause sub-retinal fluid collections, retinal detachment, hemorrhaging, and blindness, especially when it is on the macula. Accordingly, a clinician would attempt to stop blood vessel growth by administering drugs such as Lucentis™.

Additionally, VEGF can be used to overcome harmful conditions of the heart, such as to connect blood vessels with blood vessels in situations where a coronary heart vessel has been blocked by plaque. For example, a VEGF is naturally produced by the heart over time to develop collateral vessels that mitigate vessel blockages. These collaterals are created very slowly over the course of a person's lifetime. However, although this function and use of a VEGF may be encouraging, Applicant recognizes that this use is exclusively limited to connecting new blood vessels with existing blood vessels. However, there are no methods or apparatuses known in the art that facilitate connection between new blood vessels and artificial fluid conduits, such as non-blood fluid conduits.

Accordingly, some embodiments disclosed herein provide novel methods and systems for developing flow pathways using a growth factor to relieve intraocular pressure. As noted, the methods and apparatuses disclosed herein can use a growth factor, such as a VEGF. Some embodiments can use a protein, such as a VEGF, which can be impregnated or encoded with a gene. For example, a VEGF is a class of a protein that is encoded by a gene. Various types of a VEGF can be formulated and used in some embodiments.

A listing of growth factor protein families from which one or more growth factors can be used in accordance with some embodiments, include: Adrenomedullin (AM); Angiopoietin (Ang); Autocrine motility factor; Bone morphogenetic proteins (BMPs); Brain-derived neurotrophic factor (BDNF); Epidermal growth factor (EGF); Erythropoietin (EPO); Fibroblast growth factor (FGF); Glial cell line-derived neurotrophic factor (GDNF); Granulocyte colony-stimulating factor (G-CSF); Granulocyte macrophage colony-stimulating factor (GM-CSF); Growth differentiation factor-9 (GDF9); Hepatocyte growth factor (HGF); Hepatoma-derived growth factor (HDGF); Insulin-like growth factor (IGF); Migration-stimulating factor; Myostatin (GDF-8); Nerve growth factor (NGF) and other neurotrophins; Platelet-derived growth factor (PDGF); Thrombopoietin (TPO); Transforming growth factor alpha (TGF-$\alpha$); Transforming growth factor beta (TGF-$\beta$); Tumor necrosis factor alpha (TNF-$\alpha$); Vascular endothelial growth factor (VEGF); Wnt Signaling Pathway; placental growth factor (P1GF); [(Foetal Bovine Somatotrophin)] (FBS); IL-1 Cofactor for IL-3 and IL-6 (activates T cells); IL-2 T-cell growth factor (stimulates IL-1 synthesis and activates B-cells and NK cells); IL-3 (stimulates production of all non-lymphoid cells); IL-4 (growth factor for activated B cells, resting T cells, and mast cells); IL-5 (induces differentiation of activated B cells and eosinophils); IL-6 (stimulates Ig synthesis and growth factor for plasma cells); IL-7 (growth factor for pre-B cells), as well as other known or developed growth factors. VEGF-related proteins can include: VEGF-A, VEGF-B, VEGF-C, VEGF-D, VEGF isoforms, or other related proteins.

Some embodiments provide that a sequence identity to a gene or protein can be at least about 80%. For example, the sequence identity can be at least about 90%. Further, in some embodiments, the sequence identity can be at least about 95%. The sequence can be of base pairs if it is a gene or DNA, or the sequence can be amino acids if it is a protein. Some embodiments can use VEGF, the protein. Sequence identities for VEGF-A, VEGF-B, VEGF-C, and VEGF-D can be those identified in FIGS. 15A-18B or as disclosed in U.S. Application Ser. No. 61/793,241, filed Mar. 15, 2013, the entirety of which is incorporated herein by reference. FIGS. 15A-15N describe amino acid sequences for isoforms of VEGF A. FIGS. 16A-16C describe amino acid sequences for isoforms of VEGF B. FIGS. 17A-17B describe an amino acid sequence for VEGF C. FIGS. 18A-18B describe an amino acid sequence for VEGF D.

FIG. 4 illustrates that, in some embodiments, the shunt 80 can be implanted such that a vascular connecting region 92 can be implanted into an area of lower pressure than the anterior chamber. For example, the area of lower pressure can be in the subconjunctival space, the suprachoroidal space, or the supraciliary space. Thus, the outflow portion or end of the implant can be implanted into the subconjunctival space, the suprachoroidal space, or the supraciliary space and with the growth factor, facilitate growth of new blood vessels such that the implant can directly connect with blood vessels in the subconjunctival space, the suprachoroidal space, and/or the supraciliary space.

In such embodiments, the ocular implant can facilitate direct the fluid interconnection with blood vessels in the subconjunctival space, the suprachoroidal space, and/or the supraciliary space, much further beyond simply permitting diffusion into these areas. For embodiments in which the implant outflow end is positioned in the suprachoroidal or supraciliary space, the implant can be inserted through the sclera into the suprachoroidal space and the implant could be positioned over the ciliary body to over pars plana. Other ab interno methods can also be performed.

The vascular connecting region 92 can comprise a growth factor, such as one or more of those listed herein. In some embodiments, the growth factor can be disposed or coated on the vascular connecting region 92. In other embodiments, the vascular connecting region 92 can comprise a resorbable material (as discussed further below) and the growth factor can be incorporated or impregnated into the resorbable material.

As with any of the ocular implants disclosed herein, the shunt 80 can be placed by an ab interno or an ab externo method. Thus, a deployment member carrying the shunt 80 can be inserted into the cornea (in an ab interno method), the vascular connecting region 92 of the shunt 80 can be positioned in the subconjunctival space, and the deployment member can thereafter be withdrawn.

Figure 10:
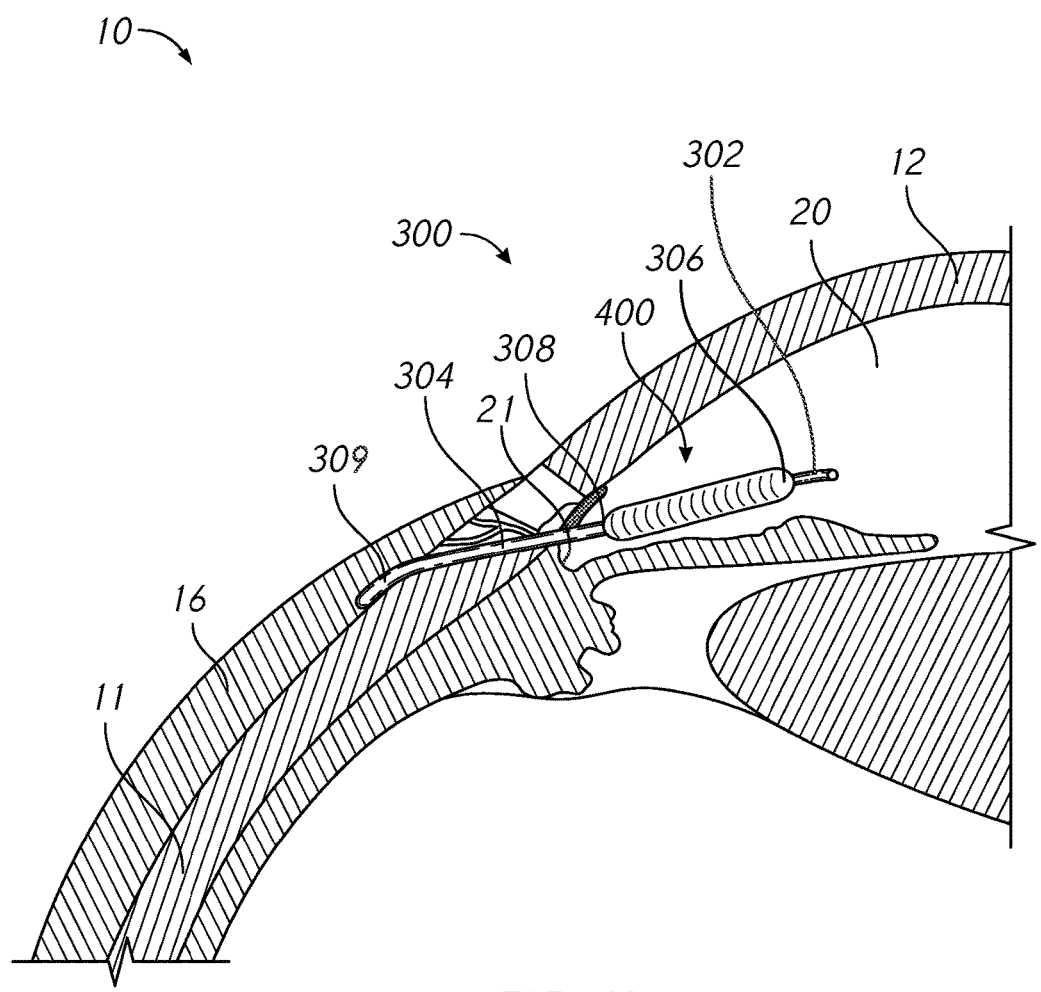
FIG. 10 illustrates placement of an implant in an eye, according to some embodiments.

For example, FIG. 10 illustrates that the implant can be delivered through the anterior chamber angle, the trabecular meshwork, and into a subconjunctival space of the eye, according to some embodiments.

After implantation of the shunt, the growth factor can begin to initiate or stimulate growth of new blood vessels 82. The new blood vessels 82 can provide an enhanced outflow pathway for aqueous humor draining from the anterior chamber.

Resorbable Materials

Figure 5:
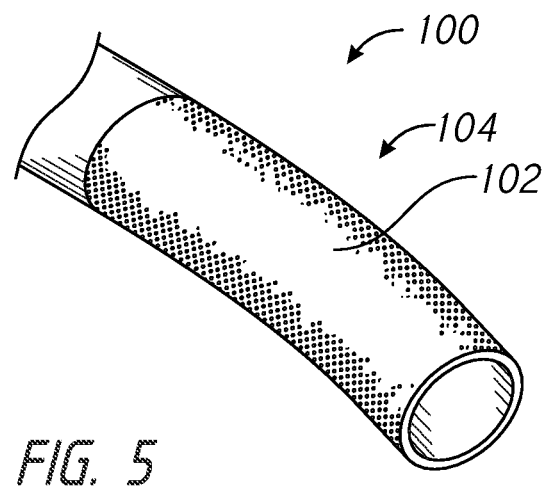
FIGS. 5-6 illustrate embodiments of an outlet portion of an implant.
Figure 6:
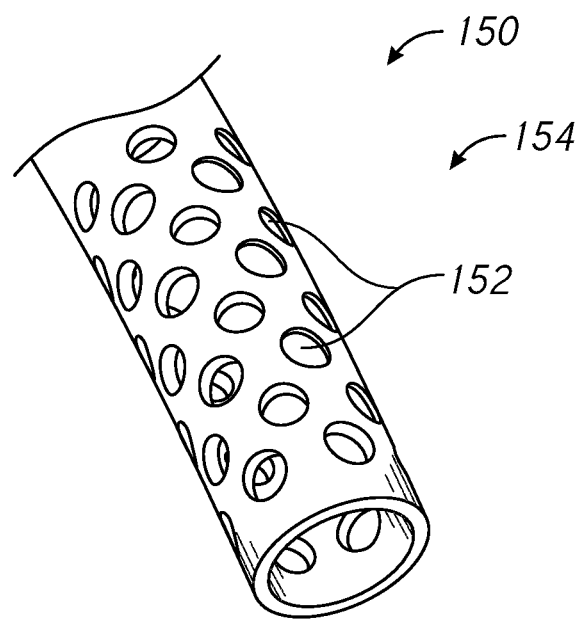

As noted above, in some embodiments, the vascular connecting region of the implant or shunt can comprise a resorbable portion. FIGS. 5 and 6 illustrate shunts 100, 150 that comprise an optional resorbable portion 102, 152 in the vascular connecting region 104, 154. In some embodiments, the vascular connecting region 104, 154 can be entirely resorbable. For example, the resorbable portion 102, 152 can comprise a collagen. Further, in some embodiments, the resorbable portion 102, 152 can comprise the growth factor, such as VEGF or other growth factor that is configured to facilitate growth of blood vessels. For example, the resorbable portion 102, 152 can comprise a collagen that holds or is impregnated with the growth factor.

Additionally, the resorbable portion 102, 152 can extend across any length or amount of the vascular connecting region or shunt length. The resorbable portion 102, 152 of the shunt 100, 150 can comprise from about 1/10 to about 1/2 of the length of the shunt. In some embodiments, the resorbable portion 102, 152 can comprise 1/8 to about 1/3 of the length of the shunt. Additionally, the resorbable portion 102, 152 can comprise about 1/6 to about 1/4 of the length of the shunt. For example, the resorbable portion 102, 152 can comprise about 1/5 to about 1/3 of the length of the shunt.

In some embodiments, the vascular connecting region of the shunt can be only partially resorbable. For example, the shunt can have at least some non-resorbable material extending over its entire length. For example, FIG. 6 illustrates that the resorbable portion 152 can comprise a portion of the vascular connecting region 154. In some embodiments, the vascular connecting region 154 can be formed from a non-resorbable polymeric material having a series of apertures or recesses that accommodate a resorbable material, as illustrated in FIG. 6. The resorbable portion 152 can be impregnated with a growth factor, such as a VEGF, and in use, the resorbable material can be dissolved into the tissue and release the growth factor. However, the growth factor can also or alternatively be carried in a coating disposed on the non-resorbable material and/or the resorbable material such that new blood vessel growth is promoted as the coating dissolves.

In accordance with some embodiments, the resorbable material can dissolve into a region of the eye within a range of from about two weeks to about 12 weeks. Further, the resorbable material can dissolve within a range of from about four weeks to about 10 weeks. Furthermore, the resorbable material can dissolve within a range of from about six weeks to about eight weeks.

Figure 9:
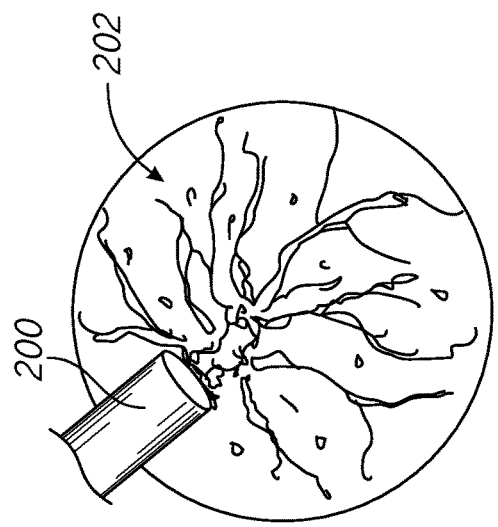
FIGS. 7-9 illustrate dissolution of a growth-factor-impregnated vascular portion of an implant and the progressive development of new blood vessels, according to some embodiments.
Figure 8:
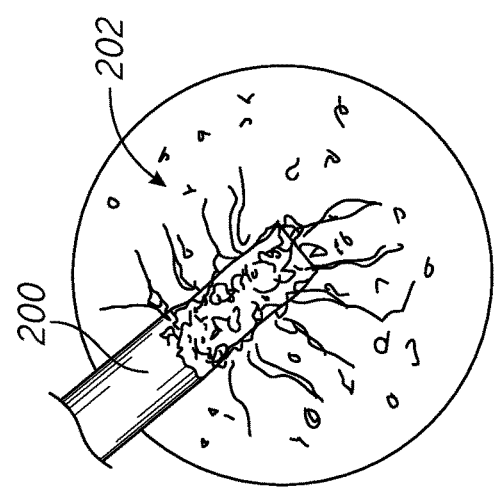
Figure 7:
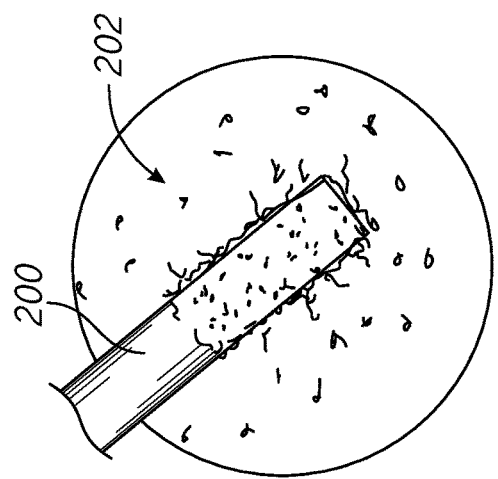

For example, FIGS. 7-9 illustrate an implant (a shunt 200) implanted into an eye and the progressive development of new blood vessel growth 202 from a growth factor that was impregnated into a resorbable portion of the shunt 200. Further, although FIGS. 7-9 illustrate resorption of a portion of the shunt 200, in some embodiments, the shunt can be coated with a growth factor to facilitate growth of new blood vessels.

Pump Mechanisms

In accordance with some embodiments, the implant can comprise a pump mechanism. The pump mechanism can be configured to draw fluid from the anterior chamber toward another location of the eye. In some embodiments, the pump mechanism can be used in combination with the growth factor, which can allow the pump mechanism to draw fluid from the anterior chamber toward newly formed or growing episcleral veins. Pump-type implants can be implanted into the eye using either the ab interno or the ab externo placement procedure.

The implant can be configured to comprise a pump mechanism coupled to one or more tubular shunts. For example, the pump mechanism can comprise an inlet and an outlet. In some embodiments, the outlet can be coupled to a tubular shunt. Further, in some embodiments, the inlet can be coupled to a tubular shunt. Furthermore, in some embodiments, each of the inlet and the outlet can be coupled to a respective tubular shunt. The use of tubular shunts and combination with the pump mechanism can enable embodiments of the ocular implant to position the pump mechanism at a location that permits the most effective use of the pump mechanism. In addition, such embodiments can advantageously collect and/or distribute the aqueous humor to any location regardless of the location of the pump mechanism.

In some embodiments, the pump mechanism can be positioned within the anterior chamber (e.g., see FIGS. 4 and 10) or outside of the anterior chamber, such as in the subconjunctival space (e.g., see FIGS. 13-14), the suprachoroidal space, and/or the supraciliary space.

In some embodiments, the position or location of the pump mechanism can advantageously be independent of the outflow location for the implant, thereby allowing the outflow portion of the implant to utilize a growth factor to stimulate growth of new blood vessels. Thus, the pump mechanism can be positioned in a variety of locations depending on the desired pump actuation (whether e.g., the pump is actuated mechanically or by a radiofrequency (RF)) and the outflow portion of the implant can extend into the subconjunctival space, the suprachoroidal space, or supraciliary space.

For example, the pump mechanism can be placed in the subconjunctival space and an outflow shunt, coupled to the outlet of the pump mechanism, can extend into the subconjunctival space, the suprachoroidal space, or supraciliary space. In such embodiments, an inlet of the pump mechanism can be coupled to an inflow shunt that extends into the anterior chamber.

Further, the pump mechanism can be placed in the anterior chamber and an outflow shunt, coupled to the outlet of the pump mechanism, can extend into the subconjunctival space, the suprachoroidal space, or supraciliary space.

Furthermore, the pump mechanism can be placed in the suprachoroidal space or supraciliary space and an outflow shunt, coupled to the outlet of the pump mechanism, can extend into the subconjunctival space, the suprachoroidal space, or supraciliary space. In such embodiments, an inlet of the pump mechanism can be coupled to an inflow shunt that extends into the anterior chamber.

In any of the above-noted placement combinations, the ocular implant can optionally incorporate other structural components or features disclosed herein, such as growth factors, resorbability, valves, or pump mechanism features.

Referring now to FIG. 10, the pump can be interconnected with a shunt. FIG. 10 illustrates an implant 300 having a pump mechanism 400 coupled to an inlet portion or shunt 302 and an outlet portion or shunt 304. The inlet shunt 302 can be coupled to an inlet 306 of the pump mechanism 400, and the outlet shunt 304 can be coupled to an outlet 308 of the pump mechanism 400. The shunt 304 can comprise a vascular connecting portion 309 at the outlet 306.

Various illustrations of embodiments of a pump mechanism 400 are shown in the figures. For example, FIGS. 3, 4, 10, 11, and 12 illustrate embodiments of an ocular implant that incorporate a pump, generally referred to as element 400. FIG. 4 also illustrates a top view through the cornea.

The pump mechanism can comprise a pliable, resilient balloon-type structure. The pump mechanism can be formed into any of a variety of three-dimensional shapes, such as a cylinder or tube, a prism (such as a hollow pad having generally flat, wide faces that are spaced apart from each other at a distance much less than a width of the pad), an annulus, and combinations thereof. Further, the pump mechanism 400 can include one or more pumping chambers that are in fluid communication with one or more inlets and one or more outlets.

Figure 11:
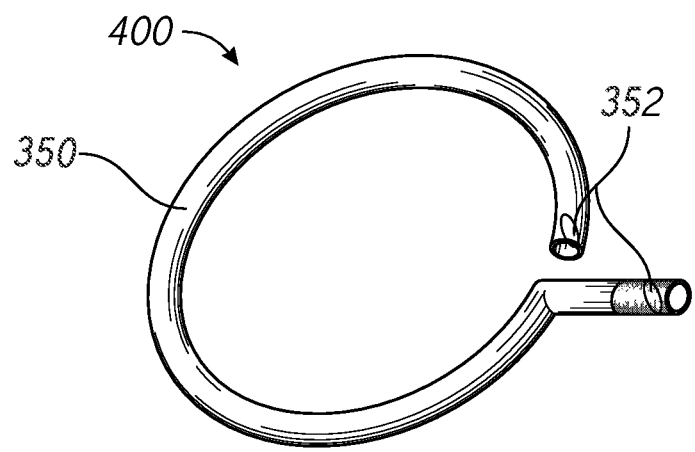
FIGS. 11-12 illustrate additional embodiments of implants incorporating a pump mechanism, according to some embodiments.

In some embodiments, the pump mechanism can have an inlet that extends into, along, or adjacent to the trabecular meshwork and/or the anterior chamber. The inlet can function similar to the atria (low pressure side) of the heart. For example, FIG. 11 illustrates an embodiment of a pump mechanism 400 that can comprise a generally annular body 350.

The pump mechanism can comprise one or more balloons having a total surface area of from about 1 mm$^2$ to about 110 mm$^2$ Some embodiments can be configured such that the surface area of the pump is from about 5 mm$^2$ to about 70 mm$^2$ Some embodiments can be configured such that the surface area of the pump is from about 8 mm$^2$ to about 50 mm$^2$ Further, the surface area of the pump is from about 10 mm$^2$ to about 30 mm$^2$ In some embodiments, the surface area of the pump is from about 12 mm$^2$ to about 20 mm$^2$.

In some embodiments, a surface of the pump mechanism can comprise one or more microstructures, such as plications or microvilli to increase the surface area of the pump mechanism 400. For example, the surface area of a balloon can be increased substantially by the use of plications (in some embodiments, the surface area can be increased by up to 1 mm$^2$, 2 mm$^2$, 3 mm$^2$, 4 mm$^2$, 5 mm$^2$, 6 mm$^2$, 7 mm$^2$, or more mm$^2$ per plication, as desired).

According to some embodiments, the surface area of the pump mechanism can be patterned after the surface area of the trabecular meshwork. For example, the surface area of the pump can be about equal to or greater than the surface area of a trabecular meshwork. Approximating the size of the pump to the size of the trabecular meshwork can enable embodiments disclosed herein to provide a rate of fluid disposal that is similar to that of the trabecular meshwork.

For example, the surface area of the trabecular meshwork can be generally approximated to the surface area of a biconcave disk having a diameter of about 12 mm (approximated using a surface area of a two-sided flat disc, $2\eta d$), which provides a total surface area of about 72 mm$^2$ It is anticipated that the surface area of a trabecular meshwork will vary, possibly by as much as 50%, from 72 mm$^2$, such that the total surface area of a trabecular meshwork can be approximated as from 36 mm$^2$ to about 108 mm$^2$.

The surface area of the pump and the surface area of a trabecular meshwork can be related as a ratio of from about 0.2:1 to about 4:1. In some embodiments, the ratio can be about 0.25:1 to about 3:1. The ratio can also be from about one third to one to about 2:1. The ratio can also be from about 0.4:1 to about 1:1. The ratio can be from about 0.5:1 to about 0.9:1. The ratio can also be from about 0.6:1 to about 0.8:1. Further, the ratio can be about 0.75:1.

In accordance with some embodiments, the pump mechanism can be operated by ocular pulse pressure (e.g., the pulse of the ophthalmic artery or blinking) or otherwise driving the pumping mechanism externally by impregnating the material and broadcasting a RF or magnetic signal. In some embodiments, the cardiac cycle can produce a pressure wave that impinges on the pump mechanism, creating a pumping effect.

In some embodiments, pump mechanisms that have larger surface areas (e.g., surface areas of at least about 20 mm$^2$) can employ ocular pulse pressure to power the pump.

Further, it has been noted that when the upper and lower eyelids are closed, the pressure of the eyelids on the ocular surface can range from 16.95±6.08 mm Hg for the upper lid and 16.11±7.27 mm Hg for the lower lid. Accordingly, the pump mechanism can be configured to compress from an expanded state when the pump mechanism undergoes a pressure of between about 5 mm Hg and about 25 mm Hg. In some embodiments, the pump mechanism can be configured to compress from the expanded state when the pump mechanism undergoes a pressure of between about 8 mm Hg and about 22 mm Hg, between about 10 mm Hg and about 20 mm Hg, between about 12 mm Hg and about 18 mm Hg, or between about 14 mm Hg and about 16 mm Hg.

The pump mechanism can be configured as an impedance pump based on the Zebrafish heart. Such embodiments can be driven externally by RF energy, magnetic energy, or by the cardiac pump cycle. External energy provided to the pump can be supplied from a user-wearable electronic component, such as glasses, headwear, an implant, or other wearable electronics. Motion within the wall of the aqueous transport member or implant may be induced by magnetic material incorporated into the wall of the aqueous transport member.

The pump mechanism can also be used in combination with one or more valves that are operative to permit fluid flow in a desired direction(s) through the pump or shunt as pulses or pressure increases are provided. For example, the implant can comprise one or more one-way valves that allow passage of fluid from the anterior chamber towards newly formed episcleral veins. In addition, in some embodiments, the one-way valve can comprise a device utilizing the principles of the embryonic Zebrafish heart, which forms a unicameral chamber.

Figure 12:
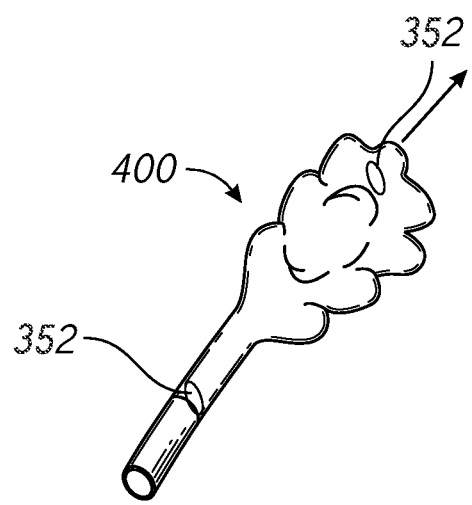

In accordance with some embodiments, an ocular implant can comprise a valve (see e.g., the elements 53 in FIGS. 2-3 and elements 352 in FIGS. 11-12). In some embodiments, an ocular implant can comprise a pump mechanism and one or two valves (see e.g., FIG. 3, 4, 10, or 12-14).

For example, in some embodiments, the inlet can comprise or be guarded by a first one-way valve. The pump mechanism can also comprise a chamber in fluid communication with the inlet. The pumping chamber can be in fluid communication with an exit that can comprise or be guarded by a second one-way valve. The valves may be mechanical and, according to some embodiments, can be built from unconventional materials. For example, the valve can comprise microvalves, such as self-regulating microfluidic microvalves and carbon fiber nanotubes, hydrogel microvalves, and other suitable mechanisms.

For example, FIG. 10 illustrates an embodiment in which the implant 300 can comprise a valve. For example, the implant 300 illustrated in FIG. 10 can comprise a valve at the inlet 302 and at the inlet 308. Any valve used in such embodiments can be a one-way valve.

According to some embodiments, pumping mechanisms and intraocular pressure sensors can be used such as those disclosed in U.S. Pat. Nos. 6,981,958, 6,638,239, 7,678,065, 7,387,500, and 8,142,364, and U.S. Patent Publication Nos. 2010/0056979 and 2012/0259195, the entireties of each of which are incorporated by reference herein. Further, some commercially available pumps can be used, such as the Zebrafish™ pump.

In some embodiments, methods are provided in which the trabecular meshwork of a given patient can be measured in order to select a pump size for the patient. However, some embodiments of methods comprise selecting a pump size independently of an actual measurement of a patient's trabecular meshwork.

Additional Methods of Use

Some embodiments disclosed herein provide methods for placing an intraocular implant having a resorbable portion with a growth factor impregnated therein for the purposes of treating glaucoma. For example, a portion of the implant can extend from the anterior chamber to the episcleral surface of the eye, on top of the sclera. In some embodiments, the placement of the implant can be subconjunctival. Further, in some embodiments, the implant can extend to subtenon placement.

Figure 13:
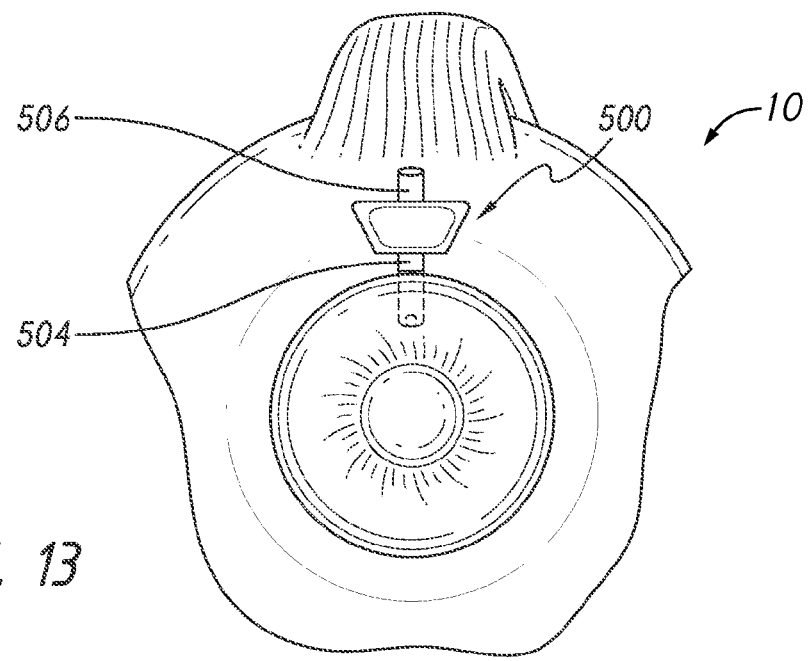
FIGS. 13-14 illustrate front and cross-sectional views of an eye in which an implant has been placed, according to some embodiments.
Figure 14:
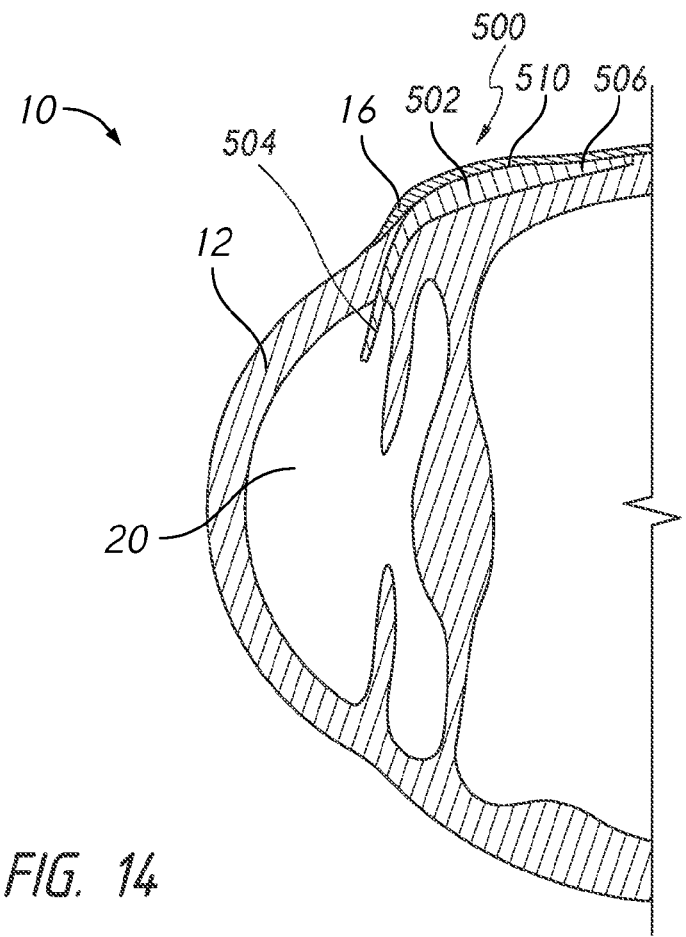

For example, FIGS. 13-14 illustrate placement of an ocular implant 500 in the subconjunctival space 510. The implant 500 can be introduced either ab interno or ab externo, and a pump mechanism 502 of the implant 500 can be positioned in the subconjunctival space. A first portion or shunt 504 can be positioned such that it extends from an inlet of the pump mechanism 502 into the anterior chamber 20 of the eye 10. Further, a second portion or shunt 506 can be positioned such that it extends from an outlet of the pump mechanism 502 to a location of lower pressure or lower pressure chamber. The lower pressure chamber can comprise at least one of a supraciliary space, an intrascleral space, a suprachoroidal space, a subconjunctival space 510, episcleral veins, aqueous collector channels, or Schlemm's canal.

In such an embodiment, the pressure exerted by the eyelid when opened and closed can serve to actuate the pump mechanism 502 in order to drive the pump mechanism 502 and withdraw aqueous humor from the anterior chamber 20.

After the implant has been placed, the growth factor can facilitate the development of new episcleral veins. Thus, according to some embodiments, the development of new episcleral veins can allow fluid drainage not just into the subconjunctival space, but also into episcleral veins.

Some embodiments provide methods and apparatuses for fluidly interconnecting episcleral veins with non-blood artificial conduits.

For example, after an implant has been placed, new episcleral veins can tend to form around the end of outflow portion of the implant. According to some embodiments, new episcleral veins can tend to form around the resorbable portion of the implant that carries or is impregnated with the growth factor. Accordingly, in due course, the resorbable portion will resorb or dissolve into the eye tissue. During this time, the new blood vessels will have formed and will extend toward the non-resorbable portion of the implant. In accordance with some aspects, the dissolution of the resorbable portion can create an open flow area (formerly occupied by the resorbable portion) that can be fluidly interconnected with new episcleral veins. Accordingly, fluid passing through the implant from the anterior chamber can have a new drainage pathway from an artificial conduit to newly formed episcleral veins.

In addition, some embodiments provide methods for treating hydrocephalus or intracranial hypertension. Hydrocephalus is a condition in which excessive fluid accumulates in the skull and exerts pressure on the brain. The fluid is a cerebrospinal fluid (CSF), a clear fluid that surrounds the brain and spinal cord. The excessive accumulation of CSF causes an abnormal widening of spaces in the brain, which are called ventricles. Potentially harmful pressure on the tissues of the brain can result from the widening of the ventricles.

Accordingly, in some embodiments, an implant having a growth factor can be placed such that an inflow end is positioned in an area of fluid accumulation in the skull (such as any of the first through fourth ventricles or other areas of fluid accumulation) and an outflow end is positioned distally and adjacent to local vasculature. Over time, the growth factor can stimulate vascular growth and permit the implant to be in direct fluid communication with blood vessels, thereby alleviating intracranial pressure. Thus, the implant can fluidly interconnect blood vessels with a non-blood artificial conduit to the ventricles.

In yet other applications, the implant can be placed adjacent to another structure to interconnect or improve fluid communication between the structure and the vascular system. In some embodiments, the implant can be placed at a bypass. For example, the bypass can comprise a percutaneous bypass, a femoropopliteal bypass (Fem-Pop bypass) for peripheral arterial disease, or other structures.

Accordingly, the apparatus and methods discussed herein are not limited to the deployment and use of a medical device within the eye, but may include any number of further treatment applications. Other treatment sites may include areas or regions of the body including any hollow anatomical structures.

Some embodiments of the implant described herein can incorporate one or more features of implants and/or implant deployment systems The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the inventions have been described, these have been presented by way of example only, and are not intended to limit the scope of the inventions. Indeed, the novel methods and systems described herein may be embodied in a variety of other forms without departing from the spirit thereof. The accompanying claims and their equivalents are intended to cover such forms or modifications as would fall within the scope and spirit of the inventions.

What is claimed is:

1. An intraocular implant comprising:
   a tubular member having an inlet region configured to extend into an anterior chamber of an eye, and a vascular connecting outlet region extending along a portion of the tubular member and configured to extend into an outflow space adjacent to a blood-carrying vessel in a subconjunctival space or along an episcleral surface of the eye; and
   a growth factor carried by the vascular connecting outlet region for stimulating growth of new blood vessels between the vascular connecting region and the blood-carrying vessel.

2. The implant of claim 1, wherein the vascular connecting region comprises at least half of a length of the tubular member.

3. The implant of claim 1, wherein the vascular connecting region comprises at least a third of a length of the tubular member.

4. The implant of claim 1, wherein the vascular connecting region comprises less than a fifth of a length of the tubular member.

5. The implant of claim 1, wherein the vascular connecting region comprises a plurality of recesses configured to carry the growth factor therein.

6. The implant of claim 1, wherein the growth factor comprises a vascular growth factor.

7. The implant of claim 6, wherein the growth factor comprises a VEGF.

8. The implant of claim 7, wherein the growth factor comprises a VEGF-A, VEGF-B, VEGF-C, or VEGF-D.

9. The implant of claim 1, wherein the vascular connecting region comprises a resorbable material and a least a portion of the growth factor.

10. The implant of claim 1, wherein the growth factor comprises a coating on the vascular connecting region.

11. The implant of claim 1, further comprising a pump for urging fluid through the implant.

12. The implant of claim 11, wherein the pump has a pumping chamber that defines a pumping surface area of from 1 mm$^2$ to 40 mm$^2$.

13. The implant of claim 11, wherein the pump is configured to operate using ocular pulse pressure.

14. The implant of claim 1, further comprising a one-way valve for facilitating fluid flow through the implant.

15. The implant of claim 1, further comprising a pump and first and second one-way valves, the pump having a pump body inlet and a pump body outlet, the tubular member coupled to the pump body outlet, wherein the first one-way valve permits flow into the pump body inlet and the second one-way valve restricts retrograde flow into the pump body outlet.

16. A method of deploying an intraocular implant into an eye for stimulating vascular growth, the method comprising:
   inserting into the eye a deployment member carrying the implant;
   releasing the implant from the deployment member such that an inflow region of the implant resides in an anterior chamber of the eye and a vascular connecting region of the implant is positioned adjacent to a blood-carrying vessel in a subconjunctival space or along an episcleral surface of the eye, the implant having a lumen to conduct fluid therethrough, the vascular connecting region of the implant carrying a growth factor for promoting growth of blood vessels between the vascular connecting region and the blood-carrying vessel to facilitate aqueous humor outflow from the location of higher pressure into the blood-carrying vessel; and
   withdrawing the deployment member from the eye.

17. The method of claim 16, wherein the growth factor comprises a vascular growth factor.

18. The method of claim 16, wherein the growth factor comprises a VEGF.

19. The method of claim 16, wherein the location of higher pressure comprises an anterior chamber of the eye.

20. The method of claim 16, wherein the vascular connecting region comprises a resorbable material and a least a portion of the growth factor.

21. The method of claim 20, wherein the vascular connecting region comprises a non-resorbable polymeric material having a plurality of apertures extending in a direction transverse to the implant lumen, the plurality of apertures comprising a resorbable material and the growth factor disposed therein.

22. The method of claim 16, wherein the growth factor is impregnated into the vascular connecting region.

23. The method of claim 16, wherein the growth factor comprises a coating on the vascular connecting region.

* * * * *

SEQUENCE LISTING

```
<160> NUMBER OF SEQ ID NOS: 17

<210> SEQ ID NO 1
<211> LENGTH: 232
<212> TYPE: PRT
<213> ORGANISM: Homo sapiens

<400> SEQUENCE: 1

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125
```

```
Glu Cys Arg Pro Lys Lys Asp Arg Ala Arg Gln Glu Lys Lys Ser Val
            130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
                180                 185                 190

His Leu Phe Val Gln Asp Pro Gln Thr Cys Lys Cys Ser Cys Lys Asn
            195                 200                 205

Thr Asp Ser Arg Cys Lys Ala Arg Gln Leu Glu Leu Asn Glu Arg Thr
210                 215                 220

Cys Arg Cys Asp Lys Pro Arg Arg
225                 230
```

<210> SEQ ID NO 2
<211> LENGTH: 215
<212> TYPE: PRT
<213> ORGANISM: Homo sapiens

<400> SEQUENCE: 2

```
Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
                35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
            130                 135                 140

Arg Gly Lys Gly Lys Gly Gln Lys Arg Lys Arg Lys Lys Ser Arg Tyr
145                 150                 155                 160

Lys Ser Trp Ser Val Pro Cys Gly Pro Cys Ser Glu Arg Arg Lys His
                165                 170                 175

Leu Phe Val Gln Asp Pro Gln Thr Cys Lys Cys Ser Cys Lys Asn Thr
            180                 185                 190

Asp Ser Arg Cys Lys Ala Arg Gln Leu Glu Leu Asn Glu Arg Thr Cys
            195                 200                 205

Arg Cys Asp Lys Pro Arg Arg
210                 215
```

<210> SEQ ID NO 3
<211> LENGTH: 209
<212> TYPE: PRT
<213> ORGANISM: Homo sapiens

<400> SEQUENCE: 3

-continued

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                      55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
    130                 135                 140

Arg Gly Lys Gly Lys Gly Gln Lys Arg Lys Arg Lys Lys Ser Arg Pro
145                 150                 155                 160

Cys Gly Pro Cys Ser Glu Arg Arg Lys His Leu Phe Val Gln Asp Pro
                165                 170                 175

Gln Thr Cys Lys Cys Ser Cys Lys Asn Thr Asp Ser Arg Cys Lys Ala
            180                 185                 190

Arg Gln Leu Glu Leu Asn Glu Arg Thr Cys Arg Cys Asp Lys Pro Arg
            195                 200                 205

Arg

<210> SEQ ID NO 4
<211> LENGTH: 191
<212> TYPE: PRT
<213> ORGANISM: Homo sapiens

<400> SEQUENCE: 4

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                      55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
            165                 170                 175

Leu Glu Leu Asn Glu Arg Thr Cys Arg Cys Asp Lys Pro Arg Arg
            180                 185                 190

<210> SEQ ID NO 5
<211> LENGTH: 174
<212> TYPE: PRT
<213> ORGANISM: Homo sapiens

<400> SEQUENCE: 5

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Asn Pro Cys Gly
            130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Met
            165                 170

<210> SEQ ID NO 6
<211> LENGTH: 171
<212> TYPE: PRT
<213> ORGANISM: Homo sapiens

<400> SEQUENCE: 6

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
            130                 135                 140

Arg Gly Lys Gly Lys Gly Gln Lys Arg Lys Lys Ser Arg Tyr
145                 150                 155                 160

Lys Ser Trp Ser Val Cys Asp Lys Pro Arg Arg
                165                 170

<210> SEQ ID NO 7
<211> LENGTH: 191
<212> TYPE: PRT
<213> ORGANISM: Homo sapiens

<400> SEQUENCE: 7

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr Asp Ser Arg Cys Lys Ala Arg Gln
                165                 170                 175

Leu Glu Leu Asn Glu Arg Thr Cys Arg Ser Leu Thr Arg Lys Asp
            180                 185                 190

<210> SEQ ID NO 8
<211> LENGTH: 147
<212> TYPE: PRT
<213> ORGANISM: Homo sapiens

<400> SEQUENCE: 8

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80

Met Arg Cys Gly Gly Cys Cys Asn Asp Glu Gly Leu Glu Cys Val Pro
                85                  90                  95

```
Thr Glu Glu Ser Asn Ile Thr Met Gln Ile Met Arg Ile Lys Pro His
            100                 105                 110
Gln Gly Gln His Ile Gly Glu Met Ser Phe Leu Gln His Asn Lys Cys
        115                 120                 125
Glu Cys Arg Pro Lys Lys Asp Arg Ala Arg Gln Glu Lys Cys Asp Lys
    130                 135                 140
Pro Arg Arg
145

<210> SEQ ID NO 9
<211> LENGTH: 137
<212> TYPE: PRT
<213> ORGANISM: Homo sapiens

<400> SEQUENCE: 9

Met Asn Phe Leu Leu Ser Trp Val His Trp Ser Leu Ala Leu Leu Leu
1               5                   10                  15
Tyr Leu His His Ala Lys Trp Ser Gln Ala Ala Pro Met Ala Glu Gly
            20                  25                  30
Gly Gly Gln Asn His His Glu Val Val Lys Phe Met Asp Val Tyr Gln
        35                  40                  45
Arg Ser Tyr Cys His Pro Ile Glu Thr Leu Val Asp Ile Phe Gln Glu
    50                  55                  60
Tyr Pro Asp Glu Ile Glu Tyr Ile Phe Lys Pro Ser Cys Val Pro Leu
65                  70                  75                  80
Met Arg Cys Gly Gly Cys Cys Asn Asp Glu Gly Leu Glu Cys Val Pro
                85                  90                  95
Thr Glu Glu Ser Asn Ile Thr Met Gln Ile Met Arg Ile Lys Pro His
            100                 105                 110
Gln Gly Gln His Ile Gly Glu Met Ser Phe Leu Gln His Asn Lys Cys
        115                 120                 125
Glu Cys Arg Cys Asp Lys Pro Arg Arg
    130                 135

<210> SEQ ID NO 10
<211> LENGTH: 371
<212> TYPE: PRT
<213> ORGANISM: Homo sapiens

<400> SEQUENCE: 10

Met Thr Asp Arg Gln Thr Asp Thr Ala Pro Ser Pro Ser Tyr His Leu
1               5                   10                  15
Leu Pro Gly Arg Arg Arg Thr Val Asp Ala Ala Ala Ser Arg Gly Gln
            20                  25                  30
Gly Pro Glu Pro Ala Pro Gly Gly Val Glu Gly Val Gly Ala Arg
        35                  40                  45
Gly Val Ala Leu Lys Leu Phe Val Gln Leu Leu Gly Cys Ser Arg Phe
    50                  55                  60
Gly Gly Ala Val Val Arg Ala Gly Glu Ala Glu Pro Ser Gly Ala Ala
65                  70                  75                  80
Arg Ser Ala Ser Ser Gly Arg Glu Glu Pro Gln Pro Glu Glu Gly Glu
                85                  90                  95
Glu Glu Glu Glu Lys Glu Glu Glu Arg Gly Pro Gln Trp Arg Leu Gly
            100                 105                 110
Ala Arg Lys Pro Gly Ser Trp Thr Gly Glu Ala Ala Val Cys Ala Asp
        115                 120                 125
```

Ser Ala Pro Ala Ala Arg Ala Pro Gln Ala Leu Ala Arg Ala Ser Gly
        130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Asn Pro Cys Gly Pro Cys Ser Glu Arg Arg Lys His Leu Phe Val Gln
                325                 330                 335

Asp Pro Gln Thr Cys Lys Cys Ser Cys Lys Asn Thr Asp Ser Arg Cys
            340                 345                 350

Lys Ala Arg Gln Leu Glu Leu Asn Glu Arg Thr Cys Arg Cys Asp Lys
        355                 360                 365

Pro Arg Arg
    370

<210> SEQ ID NO 11
<211> LENGTH: 327
<212> TYPE: PRT
<213> ORGANISM: Homo sapiens

<400> SEQUENCE: 11

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
    50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

-continued

Ser Ala Pro Ala Ala Arg Ala Pro Gln Ala Leu Ala Arg Ala Ser Gly
            130                 135                 140

Arg Gly Gly Arg Val Ala Arg Arg Gly Ala Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
                195                 200                 205

Met Ala Glu Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Cys Asp Lys Pro Arg Arg
                325

<210> SEQ ID NO 12
<211> LENGTH: 395
<212> TYPE: PRT
<213> ORGANISM: Homo sapiens

<400> SEQUENCE: 12

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
            130                 135                 140

Arg Gly Gly Arg Val Ala Arg Arg Gly Ala Glu Glu Ser Gly Pro Pro
145                 150                 155                 160

His Ser Pro Ser Arg Arg Gly Ser Ala Ser Arg Ala Gly Pro Gly Arg

```
            165                 170                 175
Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
            210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
                260                 265                 270

Glu Cys Val Pro Thr Glu Glu Ser Asn Ile Thr Met Gln Ile Met Arg
                275                 280                 285

Ile Lys Pro His Gln Gly Gln His Ile Gly Glu Met Ser Phe Leu Gln
                290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Pro Cys Gly Pro Cys Ser Glu
                340                 345                 350

Arg Arg Lys His Leu Phe Val Gln Asp Pro Gln Thr Cys Lys Cys Ser
                355                 360                 365

Cys Lys Asn Thr Asp Ser Arg Cys Lys Ala Arg Gln Leu Glu Leu Asn
            370                 375                 380

Glu Arg Thr Cys Arg Cys Asp Lys Pro Arg Arg
385                 390                 395

<210> SEQ ID NO 13
<211> LENGTH: 412
<212> TYPE: PRT
<213> ORGANISM: Homo sapiens

<400> SEQUENCE: 13

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Gly Val Glu Gly Val Gly Ala Arg
        35                  40                  45

Gly Val Ala Leu Lys Leu Phe Val Gln Leu Leu Gly Cys Ser Arg Phe
50                  55                  60

Gly Gly Ala Val Val Arg Ala Gly Glu Ala Glu Pro Ser Gly Ala Ala
65                  70                  75                  80

Arg Ser Ala Ser Ser Gly Arg Glu Glu Pro Gln Pro Glu Glu Gly Glu
                85                  90                  95

Glu Glu Glu Glu Lys Glu Glu Glu Arg Gly Pro Gln Trp Arg Leu Gly
            100                 105                 110

Ala Arg Lys Pro Gly Ser Trp Thr Gly Glu Ala Ala Val Cys Ala Asp
        115                 120                 125

Ser Ala Pro Ala Ala Arg Ala Pro Gln Ala Leu Ala Arg Ala Ser Gly
    130                 135                 140
```

-continued

```
Arg Gly Gly Arg Val Ala Arg Gly Ala Glu Ser Gly Pro Pro
145                 150                 155                 160

His Ser Pro Ser Arg Arg Gly Ser Ala Ser Arg Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
            195                 200                 205

Met Ala Glu Gly Gly Gly Gln Asn His His Glu Val Val Lys Phe Met
210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
            275                 280                 285

Ile Lys Pro His Gln Gly Gln His Ile Gly Glu Met Ser Phe Leu Gln
290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
            355                 360                 365

Glu Arg Arg Lys His Leu Phe Val Gln Asp Pro Gln Thr Cys Lys Cys
370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 14
<211> LENGTH: 207
<212> TYPE: PRT
<213> ORGANISM: Homo sapiens

<400> SEQUENCE: 14

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
                20                  25                  30

Arg Lys Val Val Ser Trp Ile Asp Val Tyr Thr Arg Ala Thr Cys Gln
            35                  40                  45

Pro Arg Glu Val Val Val Pro Leu Thr Val Glu Leu Met Gly Thr Val
50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110
```

Glu Met Ser Leu Glu Glu His Ser Gln Cys Glu Cys Arg Pro Lys Lys
              115                 120                 125

Lys Asp Ser Ala Val Lys Pro Asp Arg Ala Ala Thr Pro His His Arg
        130                 135                 140

Pro Gln Pro Arg Ser Val Pro Gly Trp Asp Ser Ala Pro Gly Ala Pro
145                 150                 155                 160

Ser Pro Ala Asp Ile Thr His Pro Thr Pro Ala Pro Gly Pro Ser Ala
                165                 170                 175

His Ala Ala Pro Ser Thr Thr Ser Ala Leu Thr Pro Gly Pro Ala Ala
            180                 185                 190

Ala Ala Ala Asp Ala Ala Ala Ser Ser Val Ala Lys Gly Gly Ala
            195                 200                 205

<210> SEQ ID NO 15
<211> LENGTH: 188
<212> TYPE: PRT
<213> ORGANISM: Homo sapiens

<400> SEQUENCE: 15

Met Ser Pro Leu Leu Arg Arg Leu Leu Leu Ala Ala Leu Leu Gln Leu
1               5                   10                  15

Ala Pro Ala Gln Ala Pro Val Ser Gln Pro Asp Ala Pro Gly His Gln
            20                  25                  30

Arg Lys Val Val Ser Trp Ile Asp Val Tyr Thr Arg Ala Thr Cys Gln
        35                  40                  45

Pro Arg Glu Val Val Val Pro Leu Thr Val Glu Leu Met Gly Thr Val
    50                  55                  60

Ala Lys Gln Leu Val Pro Ser Cys Val Thr Val Gln Arg Cys Gly Gly
65                  70                  75                  80

Cys Cys Pro Asp Asp Gly Leu Glu Cys Val Pro Thr Gly Gln His Gln
                85                  90                  95

Val Arg Met Gln Ile Leu Met Ile Arg Tyr Pro Ser Ser Gln Leu Gly
            100                 105                 110

Glu Met Ser Leu Glu Glu His Ser Gln Cys Glu Cys Arg Pro Lys Lys
        115                 120                 125

Lys Asp Ser Ala Val Lys Pro Asp Ser Pro Arg Pro Leu Cys Pro Arg
    130                 135                 140

Cys Thr Gln His His Gln Arg Pro Asp Pro Arg Thr Cys Arg Arg Arg
145                 150                 155                 160

Cys Arg Arg Arg Ser Phe Leu Arg Cys Gln Gly Arg Gly Leu Glu Leu
                165                 170                 175

Asn Pro Asp Thr Cys Arg Cys Arg Lys Leu Arg Arg
            180                 185

<210> SEQ ID NO 16
<211> LENGTH: 419
<212> TYPE: PRT
<213> ORGANISM: Homo sapiens

<400> SEQUENCE: 16

Met His Leu Leu Gly Phe Phe Ser Val Ala Cys Ser Leu Leu Ala Ala
1               5                   10                  15

Ala Leu Leu Pro Gly Pro Arg Glu Ala Pro Ala Ala Ala Ala Ala Phe
            20                  25                  30

Glu Ser Gly Leu Asp Leu Ser Asp Ala Glu Pro Asp Ala Gly Glu Ala
                35                  40                  45

Thr Ala Tyr Ala Ser Lys Asp Leu Glu Glu Gln Leu Arg Ser Val Ser
 50                  55                  60

Ser Val Asp Glu Leu Met Thr Val Leu Tyr Pro Glu Tyr Trp Lys Met
 65                  70                  75                  80

Tyr Lys Cys Gln Leu Arg Lys Gly Gly Trp Gln His Asn Arg Glu Gln
                 85                  90                  95

Ala Asn Leu Asn Ser Arg Thr Glu Glu Thr Ile Lys Phe Ala Ala Ala
                100                 105                 110

His Tyr Asn Thr Glu Ile Leu Lys Ser Ile Asp Asn Glu Trp Arg Lys
                115                 120                 125

Thr Gln Cys Met Pro Arg Glu Val Cys Ile Asp Val Gly Lys Glu Phe
130                 135                 140

Gly Val Ala Thr Asn Thr Phe Phe Lys Pro Pro Cys Val Ser Val Tyr
145                 150                 155                 160

Arg Cys Gly Gly Cys Cys Asn Ser Glu Gly Leu Gln Cys Met Asn Thr
                165                 170                 175

Ser Thr Ser Tyr Leu Ser Lys Thr Leu Phe Glu Ile Thr Val Pro Leu
                180                 185                 190

Ser Gln Gly Pro Lys Pro Val Thr Ile Ser Phe Ala Asn His Thr Ser
                195                 200                 205

Cys Arg Cys Met Ser Lys Leu Asp Val Tyr Arg Gln Val His Ser Ile
                210                 215                 220

Ile Arg Arg Ser Leu Pro Ala Thr Leu Pro Gln Cys Gln Ala Ala Asn
225                 230                 235                 240

Lys Thr Cys Pro Thr Asn Tyr Met Trp Asn Asn His Ile Cys Arg Cys
                245                 250                 255

Leu Ala Gln Glu Asp Phe Met Phe Ser Ser Asp Ala Gly Asp Asp Ser
                260                 265                 270

Thr Asp Gly Phe His Asp Ile Cys Gly Pro Asn Lys Glu Leu Asp Glu
                275                 280                 285

Glu Thr Cys Gln Cys Val Cys Arg Ala Gly Leu Arg Pro Ala Ser Cys
            290                 295                 300

Gly Pro His Lys Glu Leu Asp Arg Asn Ser Cys Gln Cys Val Cys Lys
305                 310                 315                 320

Asn Lys Leu Phe Pro Ser Gln Cys Gly Ala Asn Arg Glu Phe Asp Glu
                325                 330                 335

Asn Thr Cys Gln Cys Val Cys Lys Arg Thr Cys Pro Arg Asn Gln Pro
            340                 345                 350

Leu Asn Pro Gly Lys Cys Ala Cys Glu Cys Thr Glu Ser Pro Gln Lys
                355                 360                 365

Cys Leu Leu Lys Gly Lys Lys Phe His His Gln Thr Cys Ser Cys Tyr
            370                 375                 380

Arg Arg Pro Cys Thr Asn Arg Gln Lys Ala Cys Glu Pro Gly Phe Ser
385                 390                 395                 400

Tyr Ser Glu Glu Val Cys Arg Cys Val Pro Ser Tyr Trp Lys Arg Pro
                405                 410                 415

Gln Met Ser

<210> SEQ ID NO 17
<211> LENGTH: 354
<212> TYPE: PRT

<213> ORGANISM: Homo sapiens

<400> SEQUENCE: 17

Met Tyr Arg Glu Trp Val Val Asn Val Phe Met Met Leu Tyr Val
1               5                   10                  15

Gln Leu Val Gln Gly Ser Ser Asn Glu His Gly Pro Val Lys Arg Ser
            20                  25                  30

Ser Gln Ser Thr Leu Glu Arg Ser Glu Gln Ile Arg Ala Ala Ser
        35                  40                  45

Ser Leu Glu Glu Leu Leu Arg Ile Thr His Ser Glu Asp Trp Lys Leu
    50                  55                  60

Trp Arg Cys Arg Leu Arg Leu Lys Ser Phe Thr Ser Met Asp Ser Arg
65                  70                  75                  80

Ser Ala Ser His Arg Ser Thr Arg Phe Ala Ala Thr Phe Tyr Asp Ile
            85                  90                  95

Glu Thr Leu Lys Val Ile Asp Glu Gly Trp Gln Arg Thr Gln Cys Ser
            100                 105                 110

Pro Arg Glu Thr Cys Val Glu Val Ala Ser Glu Leu Gly Lys Ser Thr
        115                 120                 125

Asn Thr Phe Phe Lys Pro Pro Cys Val Asn Val Phe Arg Cys Gly Gly
    130                 135                 140

Cys Cys Asn Glu Glu Ser Leu Ile Cys Met Asn Thr Ser Thr Ser Tyr
145                 150                 155                 160

Ile Ser Lys Gln Leu Phe Glu Ile Ser Val Pro Leu Thr Ser Val Pro
            165                 170                 175

Glu Leu Val Pro Val Lys Val Ala Asn His Thr Gly Cys Lys Cys Leu
            180                 185                 190

Pro Thr Ala Pro Arg His Pro Tyr Ser Ile Ile Arg Arg Ser Ile Gln
        195                 200                 205

Ile Pro Glu Glu Asp Arg Cys Ser His Ser Lys Lys Leu Cys Pro Ile
210                 215                 220

Asp Met Leu Trp Asp Ser Asn Lys Cys Lys Cys Val Leu Gln Glu Glu
225                 230                 235                 240

Asn Pro Leu Ala Gly Thr Glu Asp His Ser His Leu Gln Glu Pro Ala
            245                 250                 255

Leu Cys Gly Pro His Met Met Phe Asp Glu Asp Arg Cys Glu Cys Val
            260                 265                 270

Cys Lys Thr Pro Cys Pro Lys Asp Leu Ile Gln His Pro Lys Asn Cys
        275                 280                 285

Ser Cys Phe Glu Cys Lys Glu Ser Leu Glu Thr Cys Cys Gln Lys His
    290                 295                 300

Lys Leu Phe His Pro Asp Thr Cys Ser Cys Glu Asp Arg Cys Pro Phe
305                 310                 315                 320

His Thr Arg Pro Cys Ala Ser Gly Lys Thr Ala Cys Ala Lys His Cys
            325                 330                 335

Arg Phe Pro Lys Glu Lys Arg Ala Ala Gln Gly Pro His Ser Arg Lys
            340                 345                 350

Asn Pro